US012576247B2

(12) United States Patent
Taylor et al.

(10) Patent No.: US 12,576,247 B2
(45) Date of Patent: *Mar. 17, 2026

(54) INTRODUCER SHEATH SYSTEMS AND METHODS

(71) Applicant: Cultiv8 Medical, LLC, Minneapolis, MN (US)

(72) Inventors: Kyle P. Taylor, Greenfield, MN (US); Michael Brenzel, St. Paul, MN (US); David Matthew Costello, Delano, MN (US); Robert E. Atkinson, White Bear Lake, MN (US)

(73) Assignee: Cultiv8 Medical, LLC, Minneapolis, MN (US)

( * ) Notice: Subject to any disclaimer, the term of this patent is extended or adjusted under 35 U.S.C. 154(b) by 97 days.

This patent is subject to a terminal disclaimer.

(21) Appl. No.: 18/644,816

(22) Filed: Apr. 24, 2024

(65) Prior Publication Data

US 2024/0358975 A1    Oct. 31, 2024

Related U.S. Application Data

(60) Provisional application No. 63/591,928, filed on Oct. 20, 2023, provisional application No. 63/512,740, (Continued)

(51) Int. Cl.
*A61M 39/06* (2006.01)
*A61M 25/00* (2006.01)
(Continued)

(52) U.S. Cl.
CPC .... *A61M 25/0662* (2013.01); *A61M 25/0097* (2013.01); *A61M 29/00* (2013.01);
(Continued)

(58) Field of Classification Search
CPC .......... A61M 25/0662; A61M 25/0097; A61M 29/00; A61M 39/0613; A61M 2039/062;
(Continued)

(56) References Cited

U.S. PATENT DOCUMENTS 4,540,411 A    9/1985   Bodicky
4,580,573 A    4/1986   Quinn
(Continued)

FOREIGN PATENT DOCUMENTS

AU        2020279750 B2      7/2023

OTHER PUBLICATIONS

International Search Report and Written Opinion issued for PCT Application No. PCT/US2024/025981, mailed Aug. 16, 2024 (11 pages).

*Primary Examiner* — Tan-Uyen T Ho
*Assistant Examiner* — Bridget E. Rabaglia
(74) *Attorney, Agent, or Firm* — Bookoff McAndrews, PLLC

(57) ABSTRACT

Introducer sheath systems including a pressure regulator operably coupled to a hemostatic valve, wherein the pressure regulator includes a chamber filled with a gas that is fluidly isolated from the hemostatic valve. The introducer sheath systems may include a tubular sheath, a hub assembly, and a dilator disposed therein connected to a proximal end of the sheath; the hub assembly including a housing and a hemostatic valve disposed therein; a pressure regulator connected to the hub and in fluid communication with the hemostatic valve; and a sealed chamber defined by the pressure regulator, the chamber having an interior, wherein the interior of the chamber is filled with a gas that is fluidly isolated from the hemostatic valve.

20 Claims, 25 Drawing Sheets

Related U.S. Application Data filed on Jul. 10, 2023, provisional application No. 63/498,637, filed on Apr. 27, 2023.

(51) Int. Cl.
  *A61M 25/06*        (2006.01)
  *A61M 29/00*        (2006.01)
(52) U.S. Cl.
  CPC ... *A61M 39/0613* (2013.01); *A61M 2039/062* (2013.01); *A61M 2039/0626* (2013.01); *A61M 2039/0673* (2013.01); *A61M 2205/0216* (2013.01); *A61M 2205/3331* (2013.01); *A61M 2205/583* (2013.01)
(58) Field of Classification Search
  CPC .. A61M 2039/0626; A61M 2039/0673; A61M 2205/0216; A61M 2205/3331; A61M 2205/583
  See application file for complete search history.

(56) References Cited

U.S. PATENT DOCUMENTS

| 5,071,411 A | | 12/1991 | Hillstead |
| 5,161,773 A | * | 11/1992 | Tower ............... A61M 39/0613 251/5 |
| 5,360,417 A | | 11/1994 | Gravener et al. |
| 5,401,248 A | | 3/1995 | Bencini |
| 5,556,387 A | | 9/1996 | Mollenauer et al. |
| 5,782,817 A | | 7/1998 | Franzel et al. |
| 5,871,474 A | | 2/1999 | Hermann et al. |
| 5,895,376 A | | 4/1999 | Schwartz et al. |
| 5,989,233 A | | 11/1999 | Yoon |
| 6,221,057 B1 | | 4/2001 | Schwartz et al. |
| 6,238,373 B1 | | 5/2001 | de la Torre et al. |
| 7,673,846 B2 | | 3/2010 | Jennings et al. |
| 8,002,749 B2 | | 8/2011 | Macatangay et al. |
| 8,118,784 B2 | | 2/2012 | Molgaard-Nielsen |
| 8,137,321 B2 | | 3/2012 | Argentine |
| 8,235,943 B2 | | 8/2012 | Breznock et al. |
| 8,235,946 B2 | | 8/2012 | Molgaard-Nielsen |
| 8,858,504 B2 | | 10/2014 | Nielsen |
| 9,314,605 B2 | | 4/2016 | Arcaro et al. |
| 9,333,332 B2 | | 5/2016 | Eisenkolb et al. |
| 9,440,059 B2 | | 9/2016 | Moore |
| 9,592,372 B2 | | 3/2017 | Myers |
| 9,884,175 B2 | | 2/2018 | Furnish et al. |
| 10,155,104 B2 | | 12/2018 | Arcaro et al. |
| 10,960,198 B2 | | 3/2021 | Arcaro et al. |
| 11,779,742 B2 | | 10/2023 | Chalekian et al. |
| 2003/0225379 A1 | | 12/2003 | Schaffer et al. |
| 2004/0172008 A1 | | 9/2004 | Layer |
| 2008/0142747 A1 | * | 6/2008 | Jennings ................. F16K 7/075 251/5 |
| 2011/0077591 A1 | | 3/2011 | Plicchi et al. |
| 2011/0270182 A1 | * | 11/2011 | Breznock ................ A61M 5/36 604/122 |
| 2015/0112279 A1 | * | 4/2015 | Myers ............... A61M 39/0613 604/256 |
| 2021/0146054 A1 | * | 5/2021 | Cully ................... A61K 9/0019 |
| 2021/0187269 A1 | | 6/2021 | Arcaro et al. |
| 2022/0339419 A1 | * | 10/2022 | Wang ................ A61M 39/0613 |
| 2024/0207592 A1 | | 6/2024 | Oshimizu |
| 2024/0245895 A1 | | 7/2024 | Oshimizu |
| 2025/0032767 A1 | | 1/2025 | Dunlea |
| 2025/0050071 A1 | | 2/2025 | Geist et al. |

* cited by examiner

| PRODUCT | SLOPE (PSI/mm²) | SLOPE (PSI/F) |
|---|---|---|
| GORE DRY SEAL | 0.34 | 0.75 |
| SAMPLE 1 | 0.06 | 0.14 |
| SAMPLE 2 | 0.12 | 0.26 |
| SAMPLE 3 | 0.12 | 0.26 |

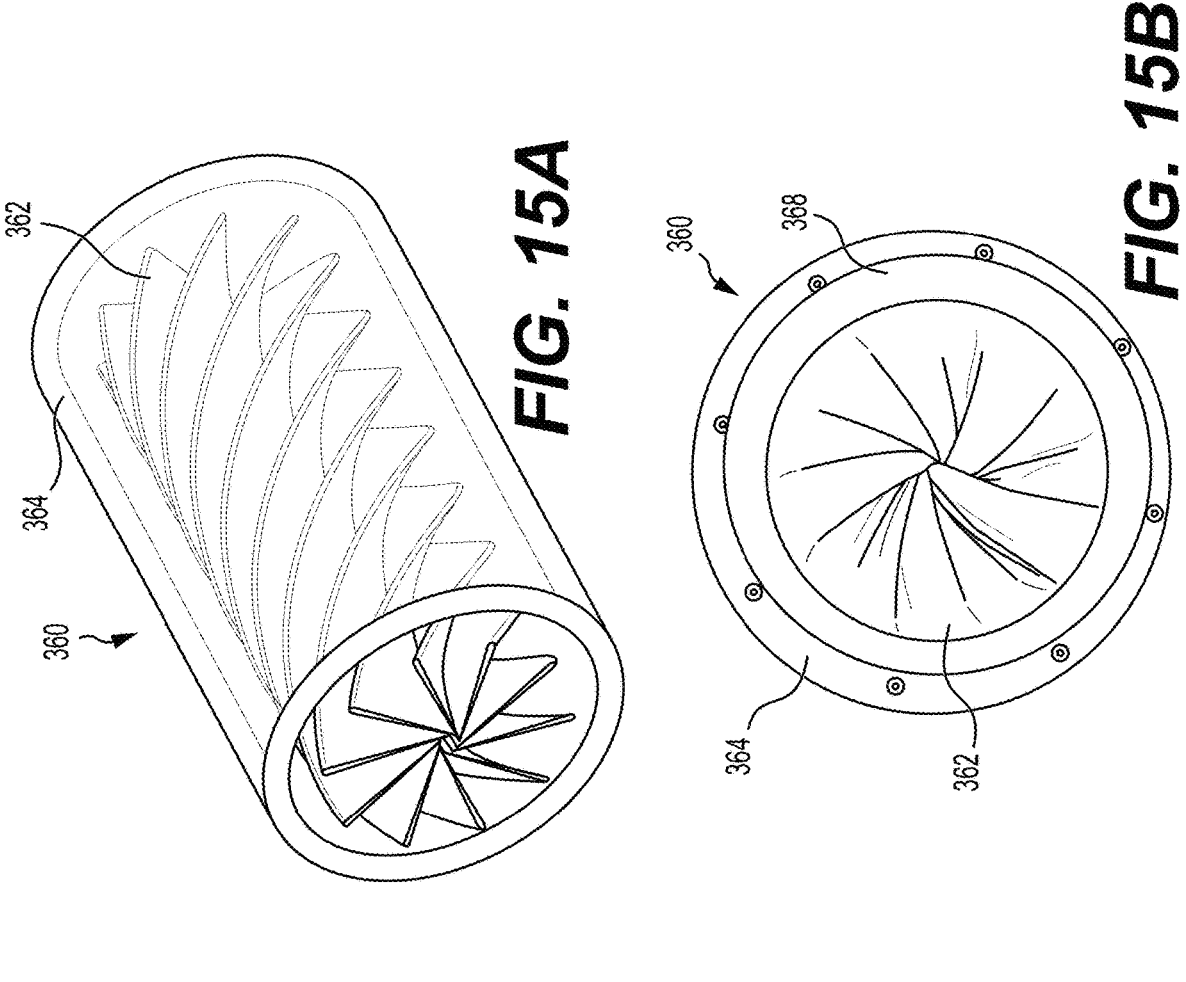
FIG. 15A
FIG. 15B
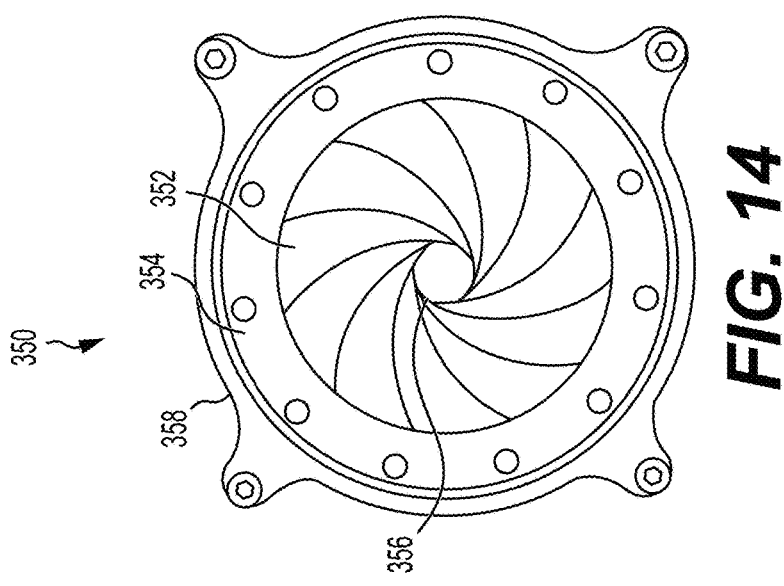
FIG. 14

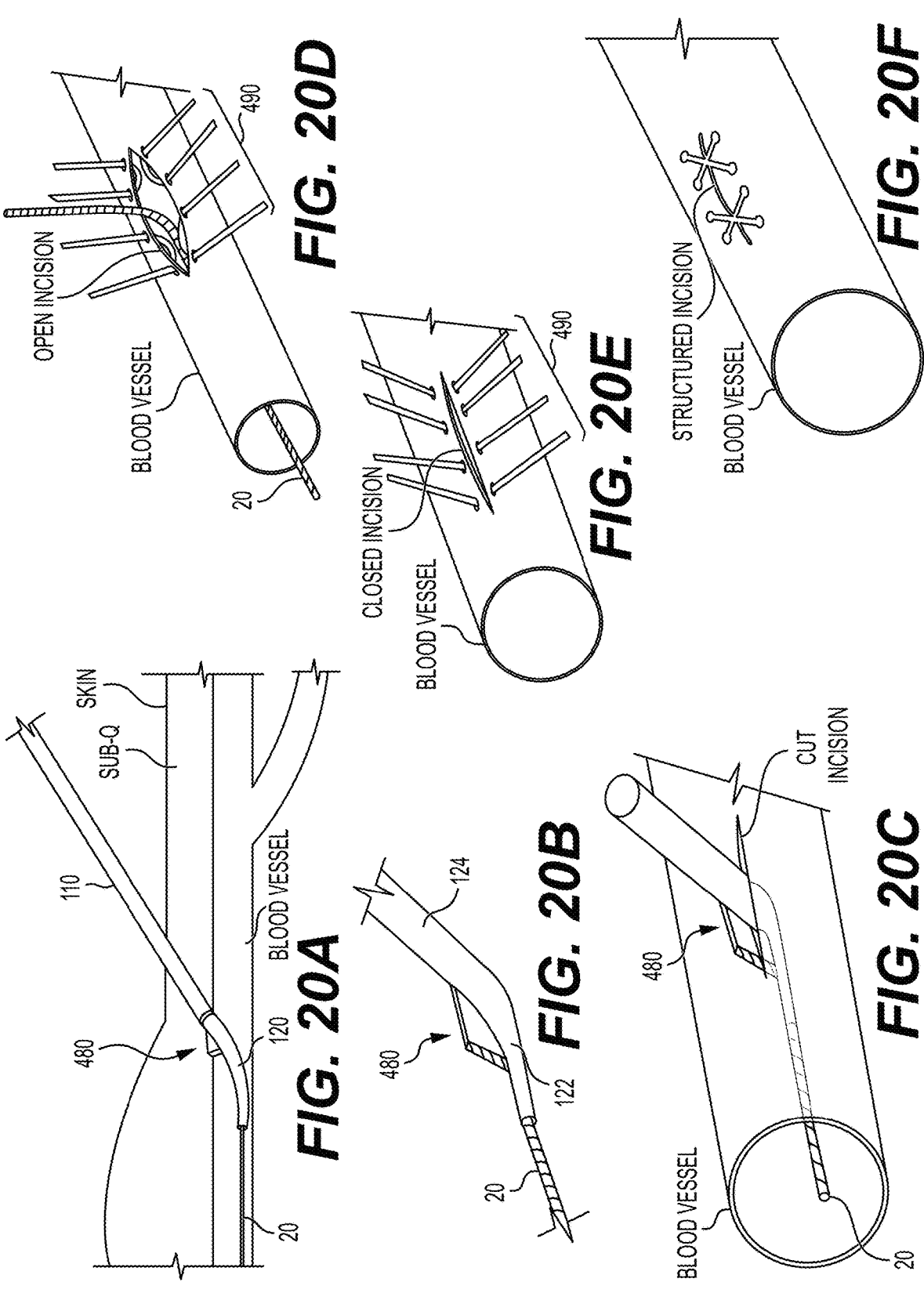

INTRODUCER SHEATH SYSTEMS AND METHODS

CROSS-REFERENCE TO RELATED APPLICATIONS

This application claims the benefit of U.S. Provisional Patent Application No. 63/498,637, filed Apr. 27, 2023; U.S. Provisional Patent Application No. 63/512,740 filed, Jul. 10, 2023; and U.S. Provisional Patent Application No. 63/591,928, filed Oct. 20, 2023, the entire disclosures of which are incorporated herein by reference.

TECHNICAL FIELD

The present disclosure generally relates to introducer sheath systems that are intended to be inserted into the vasculature to provide a conduit for introducing intravascular devices while providing a hemostatic seal to minimize blood loss. The embodiments of the present disclosure also have application to other catheter and cannula constructions and other associated clinical applications.

BACKGROUND

U.S. Pat. No. 10,960,198 to Arcaro et al. generally describes an introducer sheath containing a valve to provide a seal around devices inserted therethrough. Arcaro et al. describe a valve comprising an inner tube formed of ePTFE, surrounded by an outer tube formed of an elastomer. The space between the outer tube and the inner tube may be pressurized to collapse the inner tube around a device inserted therethrough, thus providing a seal to mitigate back bleeding. The outer tube expands from an hourglass shape as the space is pressurized, thus visually indicating when sufficient pressure is established.

The device described by Arcaro et al. generally corresponds to a commercial product called the GORE® DrySeal Flex Introducer Sheath. In use, as the pressure of the valve is increased, so is the friction around devices inserted therethrough. This is particularly significant as large bore devices, such as TAVR delivery systems, are inserted through the sheath, which causes pressure and friction to increase. Such friction may compromise movement and control of devices inserted through the valve.

SUMMARY OF THE DISCLOSURE

To improve on such, the present disclosure describes, in one embodiment, an introducer sheath system including a pressure regulator operably coupled to the valve. The pressure regulator reduces the magnitude of increased pressure as devices are inserted into the valve, and thereby mitigates the degree of increased friction, thus allowing easier movement and better control of inserted devices. The pressure regulator may utilize a compressible component that is operably coupled to the valve but fluidly isolated from the valve. The pressure regulator may comprise a fluidly isolated chamber. Examples of fluidly isolated chambers include, but are not limited to, a bladder, a diaphragm chamber, a closed-cell foam component, etc. The fluidly isolated chamber may be at least partially filled with a gas (e.g., air) to provide more compliance than the liquid (e.g., saline) used to pressurize the valve. Fluid isolation may be beneficial when using gas in a pressure regulator to avoid introducing gas into the vascular system in the event of a valve failure.

Embodiments of the introducer sheath systems described herein also provide other benefits, such as a bubble capture, alternative anchoring systems, alternative hemostatic valve designs, device brake features, etc. Such improvements are described in more detail hereinafter with reference to the drawings. The above summary is not intended to describe each and every embodiment or implementation of the present disclosure.

BRIEF DESCRIPTION OF THE DRAWINGS

The drawings illustrate example embodiments of the present disclosure and, along with the description, serve to explain the principles of the disclosure. The drawings are only illustrative of certain embodiments and do not limit the disclosure or invention.

FIG. 14 is a schematic end view of a hemostatic valve according to another alternative embodiment of the present disclosure.

FIGS. 15A and 15B are schematic perspective and end views, respectively, of a hemostatic valve according to another alternative embodiment of the present disclosure.

FIGS. 20A-20F are schematic perspective views of an alternative dilator and its use according to an alternative embodiment of the present disclosure.

Figure 1:
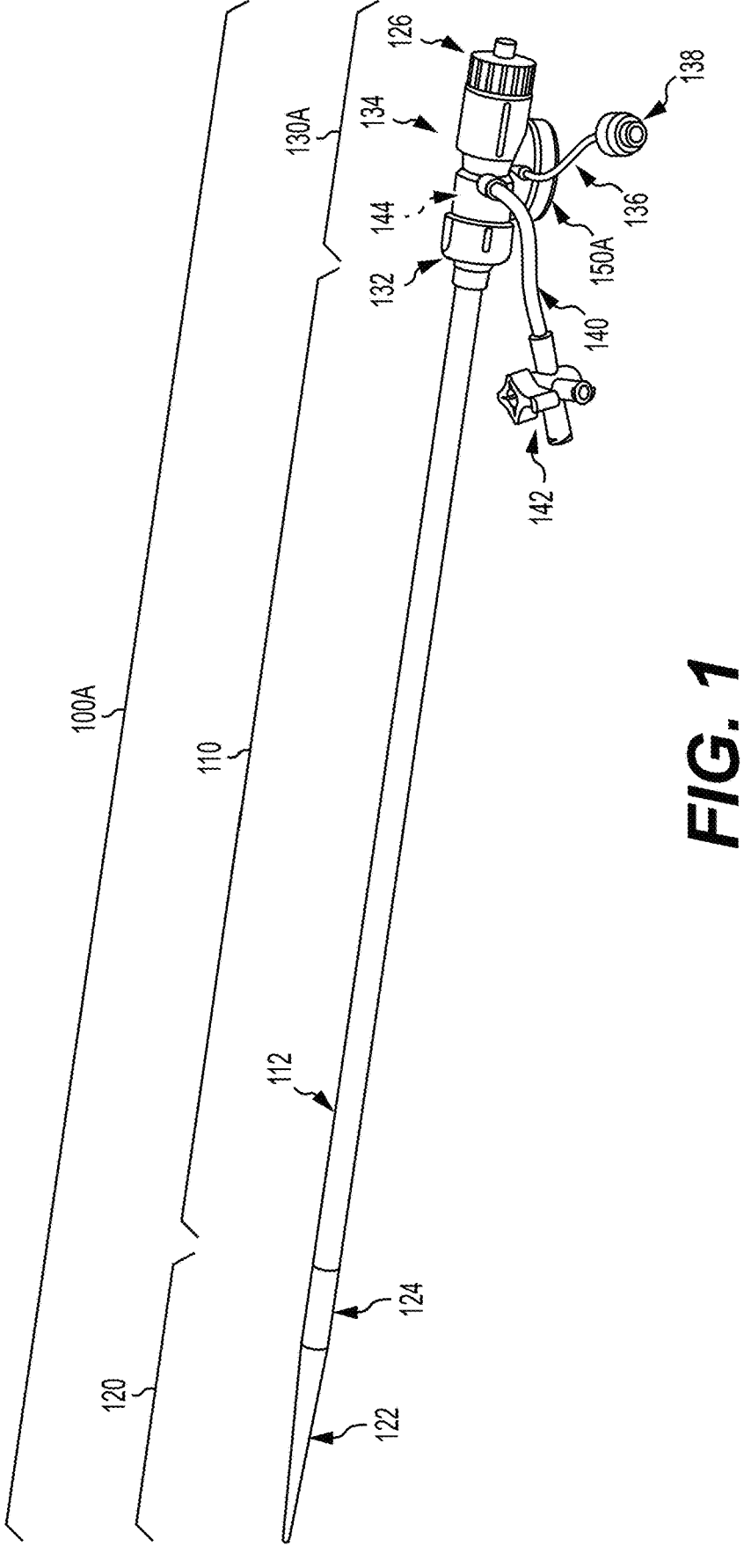
FIG. 1 is a perspective assembly view of an introducer sheath system according to an embodiment of the present disclosure.

While embodiments of the disclosure are amenable to various modifications and alternative forms, specifics thereof have been shown by way of example in the drawings and will be described in some detail. It should be understood, however, that the intention is not to limit the disclosure to the particular embodiments described. On the contrary, the intention is to cover all modifications, equivalents, and alternatives falling within the spirit and scope of the invention.

DETAILED DESCRIPTION OF EMBODIMENTS

With reference to FIG. 1, an assembly view of introducer sheath system 100A according to an embodiment of the present disclosure is shown. In general, the system 100A may include a tubular sheath body 110, a dilator 120 extending therethrough, and a main hub assembly 130A connected to a proximal end of the sheath body 110. The assembly 100A may be inserted into the vasculature as a system, with the main hub 130A remaining outside the body. Once placed, the dilator 120 may be removed to define a conduit through the hub 130A and sheath 110 into the vasculature.

The sheath body 110 may comprise, for example, a composite tube including a PTFE inner layer or liner, a stainless-steel coil disposed about the inner layer, and an outer layer (e.g., polyether-block-amide) disposed over the coil. The sheath body 110 may be connected to the main hub assembly 130A via screw-type connector 132, for example. To facilitate visualization via fluoroscopy, a radiopaque marker band may be incorporated into the distal end of the sheath body 120 between the layers thereof, for example. Although a specific composite construction of the sheath body 110 is described above, by way of example, not limitation, other composite or monolithic constructions may be employed. The sheath 110 may be available in sizes (diameters) ranging from 10 F to 26 F and lengths of 33 cm, 45 cm or 65 cm, for example.

The dilator 120 may comprise a relatively rigid LDPE tube, for example, with a tapered distal end 122, a constant diameter main body portion 124, and a proximal hub 126. The lumen of the dilator 120 extends the entire length thereof to accommodate a guide wire (e.g., 0.035" guidewire compatible, not shown), over which the assembly 100A is delivered. The main body portion 124 may have an outer diameter that closely matches the inside diameter of the sheath body 110, with a small gap to allow relative movement therebetween. The tapered distal end 122 of the dilator provides gradual dilatation of the vascular puncture site and a smooth transition from the guidewire to the sheath distal tip 112. The dilator hub 126 may include an interlocking feature that mates with, and releasably secures to, the main hub assembly 130A. To facilitate visualization via fluoroscopy, the dilator 120 may be loaded with a radiopaque material such as barium sulfate.

The main hub assembly 130A generally includes a housing 134, formed of an injection molded polymer, for example. The sheath-to-hub connector 132 may be secured to a distal aspect of the housing 134. A proximal aspect of the housing 134 may contain a hemostatic valve (not visible in this figure). Generally, the hemostatic valve provides a seal around inserted devices to minimize blood loss. The hemostatic valve may comprise a relatively rigid or non-collapsible valve body 162 and a collapsible sleeve 160 (e.g., ePTFE, FEP, or a laminate thereof) mounted at both ends to the valve body 162. The sleeve 160 may be compressed by pressurizing the space between the valve body 162 and the sleeve 160. Pressurizing the sleeve 160 may accomplished by connecting a saline-filled syringe to, and injecting saline through, a valve line 136 via a connector 138 (e.g., needleless valve, stopcock, etc.). The connector 138 associated with the valve line 136 may be configured differently than the connector 142 associated with the flush line 140 so as to avoid confusion between the connectors and mitigate human error.

The hub assembly 130A may also include a flush line 140 with a connector (e.g., 3-way stop cock) for connection to a syringe or power injector to facilitate the injection or removal of gases such as air or liquids such as saline, contrast media, etc. to/from the introducer sheath 100A and/or the vasculature. The hub housing 134 may define a transparent bubble chamber 144 to visualize bubbles that may be inadvertently introduced when inserting large devices into the hub 130A, whereby such bubbles may be removed via the flush line 140. To facilitate this, the flush line may be connected to a vertical apex of the bubble chamber 144.

The introducer sheath assembly may further include a pressure regulator 150A operably connected to the valve assembly. The pressure regulator 150A may reduce the magnitude of increased pressure in the space between the valve body 162 and the collapsible sleeve 160 as devices are inserted into the valve assembly. By reducing the magnitude of increased pressure, the pressure regulator 150A can mitigate the degree of increased friction imposed by the sleeve on devices inserted into the valve assembly. By mitigating friction, inserted devices may be freer to manipulate or otherwise move relative to the sheath assembly 100A, thus allowing better control thereof.

The pressure regulator 150A may include a housing defining or containing a sealed chamber. The outside of the sealed chamber may be in fluid communication with the valve, and the inside of the sealed chamber may be fluidly isolated from the valve. The inside of the chamber may contain a compressible component (e.g., a gas such as air) that is more compressible than the fluid (e.g., a liquid such as saline). For example, the sealed chamber may comprise a closed-cell foam wherein the inside of the cells contain air. Alternatively, a deflectable diaphragm supported by a rigid housing may define the sealed chamber, wherein the chamber is filled air. As a further alternative, the sealed chamber may comprise an air-filled bladder. Another alternative is a piston-camber arrangement wherein a plunger with a sliding seal resides within a chamber filled with air. In each case, the inside of the sealed chamber may be fluidly isolated from the valve. Fluid isolation may be beneficial when using gas in the pressure regulator to avoid introducing the gas into the vascular system in the event of a valve failure.

By way of example, not limitation, the pressure regulator 150A may be located separately and remotely from the hub 130A and connected by tubing, connected to the hub 130A via a molded orifice, or integrated into the hub 130A as shown. Further aspects of the valve and pressure regulator configuration and function are described in more detail hereinafter.

Figure 2A:
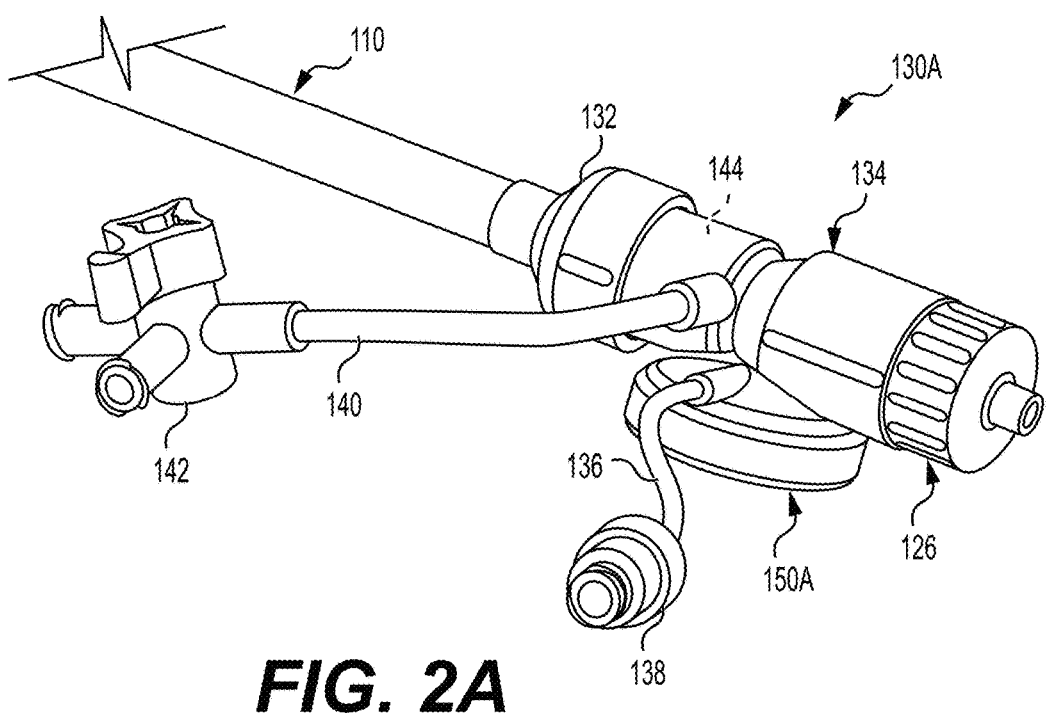
FIGS. 2A and 2B are detailed perspective views of a proximal portion of the introducer sheath system shown in FIG. 1.
Figure 2B:
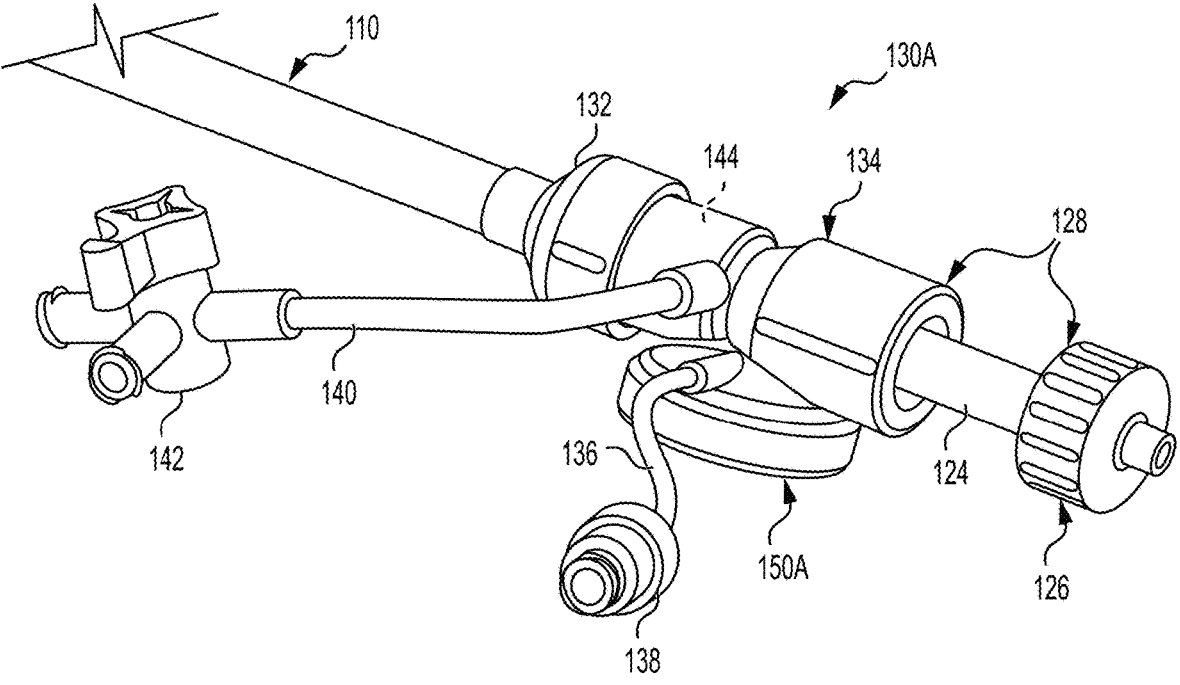

With reference to FIGS. 2A and 2B, additional detail of the interconnection between the hub 126 of the dilator 120 and the hub assembly 130A may be appreciated. The interconnection between the dilator hub 126 and the hub assembly 130A may comprise interlocking features 128 with corresponding configurations on each component that mate and lock. For example, the interlocking features 128 may comprise tabs on one component and corresponding openings on the other component, wherein the tabs are inserted into the openings and the hubs are twisted (relatively) to lock. Alternatively, the interlocking features 128 may comprise male and female threads or a snap-fit geometry. In any case, the interlocking features 128 allow the sheath system 100A to be inserted into the vasculature as a locked assembly, after which the hubs may be unlocked to remove the dilator 120 from the sheath 110 and main hub 130A.

Figure 3:
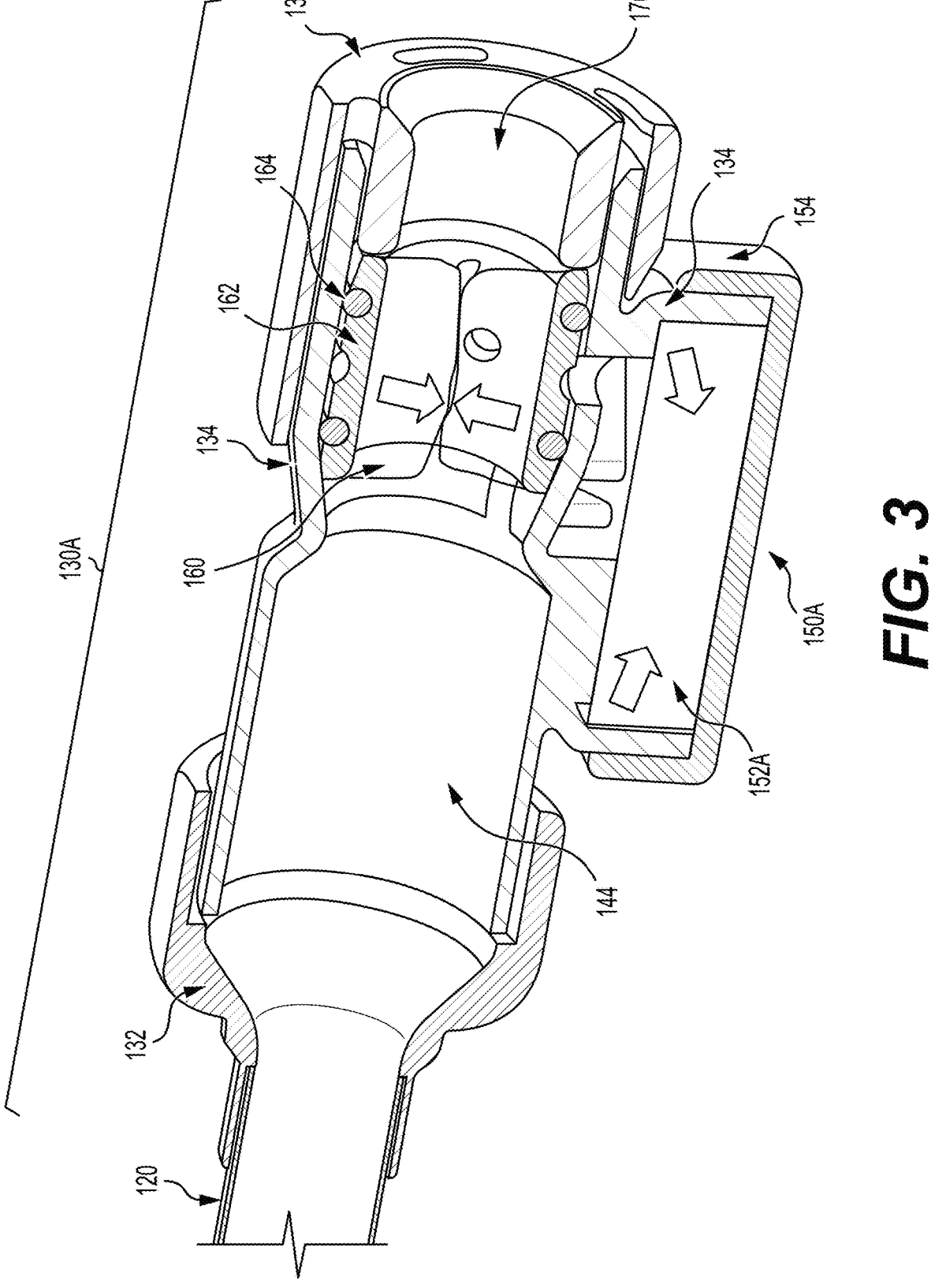
FIG. 3 is a longitudinal sectional view of the proximal portion of the introducer sheath system shown in FIG. 1.

With reference to FIG. 3, a longitudinal cross-sectional view of the hub assembly 130A is shown, from which the internal components thereof may be appreciated in more detail. The main hub 130A includes a housing 134 and cap 135 containing a valve body 162. Devices may be inserted into the hub assembly via on-axis port 170. Inside the valve body 162, a collapsible sleeve 160 resides. As mentioned previously, when the space between the relatively rigid valve body 162 and the sleeve 160 is pressurized, the sleeve 160 collapses as indicated by the bold arrows, and seals about a device or devices inserted therein.

At the same time, the pressure regulator 150A, which in this example is a closed-cell foam disc 152A contained in the housing 134 by cap 154, compresses as indicated by the bold arrows. The closed-cell foam disc may comprise geometries and sizes other than those illustrated. A fluid path may be defined by the housing 134 to provide fluid communication from the pressurized space exterior of the sleeve 160 to the space containing the closed-cell foam disc 152A. However, because the foam disc 152A is closed cell, the interior of such is fluidly isolated from the pressurized space around the sleeve 160.

Figure 3B:
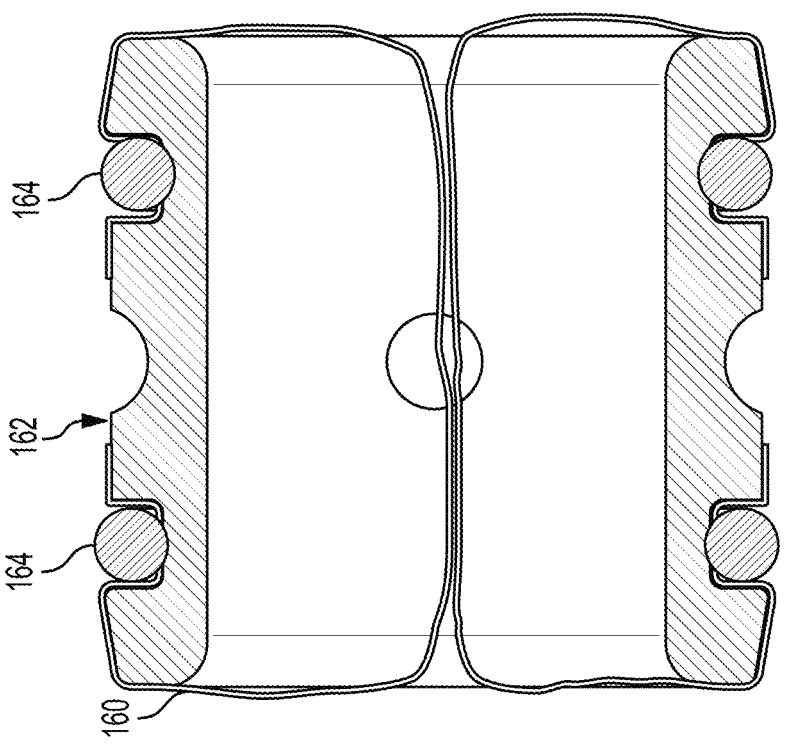
FIGS. 3A and 3B are longitudinal cross-sectional views of example embodiments of a valve assembly shown in FIG. 3.
Figure 3A:
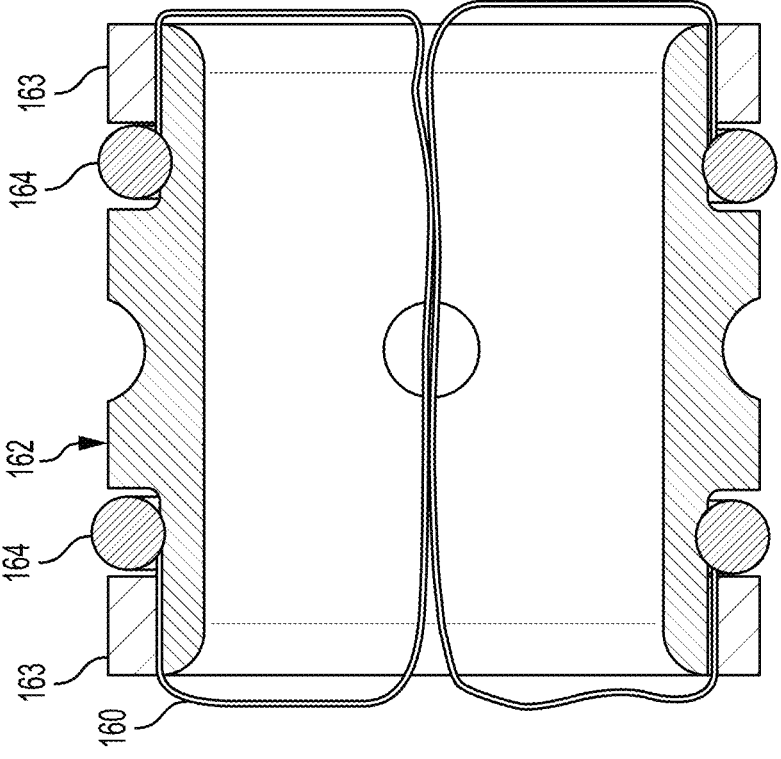

With reference to FIGS. 3A and 3B, two embodiments of a valve assembly are shown in more detail in longitudinal cross-sectional views. In each embodiment, the valve assembly includes a relatively rigid or non-collapsible valve body 162 and a relatively collapsible valve sleeve 160. The collapsible sleeve 160 may comprise a ePTFE, densified ePTFE, or an ePTFE laminate such as FEP laminated over ePTFE, wherein the ePTFE is in a tubular form or a sheet form subsequently rolled into a tube. The valve body 162 may comprise an injection molded polymer. To attach the valve sleeve 160 to the valve body 162 and provide both a mechanical and fluid-sealed connection therebetween, the ends of the sleeve 160 may be wrapped or inverted around the ends of the valve body 162 and secured in place utilizing a pair of silicone O-rings 164, for example. The O-rings 164 may be disposed in a notch, as shown, and the ends of the sleeve 160 may extend into all or a portion of the notch to provide a mechanical interlock. Optionally, polymer rings 163 may be placed over the ends of the sleeve 160 and adhesively or thermally boded to the valve body 162. Adhesive or thermal bonds between the valve sleeve 160 and the valve body 162 may be placed at the end faces of the valve body 162 adjacent the peripheral edges thereof, and/or the top face of the valve body 162 adjacent the ends of the sleeve 160, for example.

Figure 4:
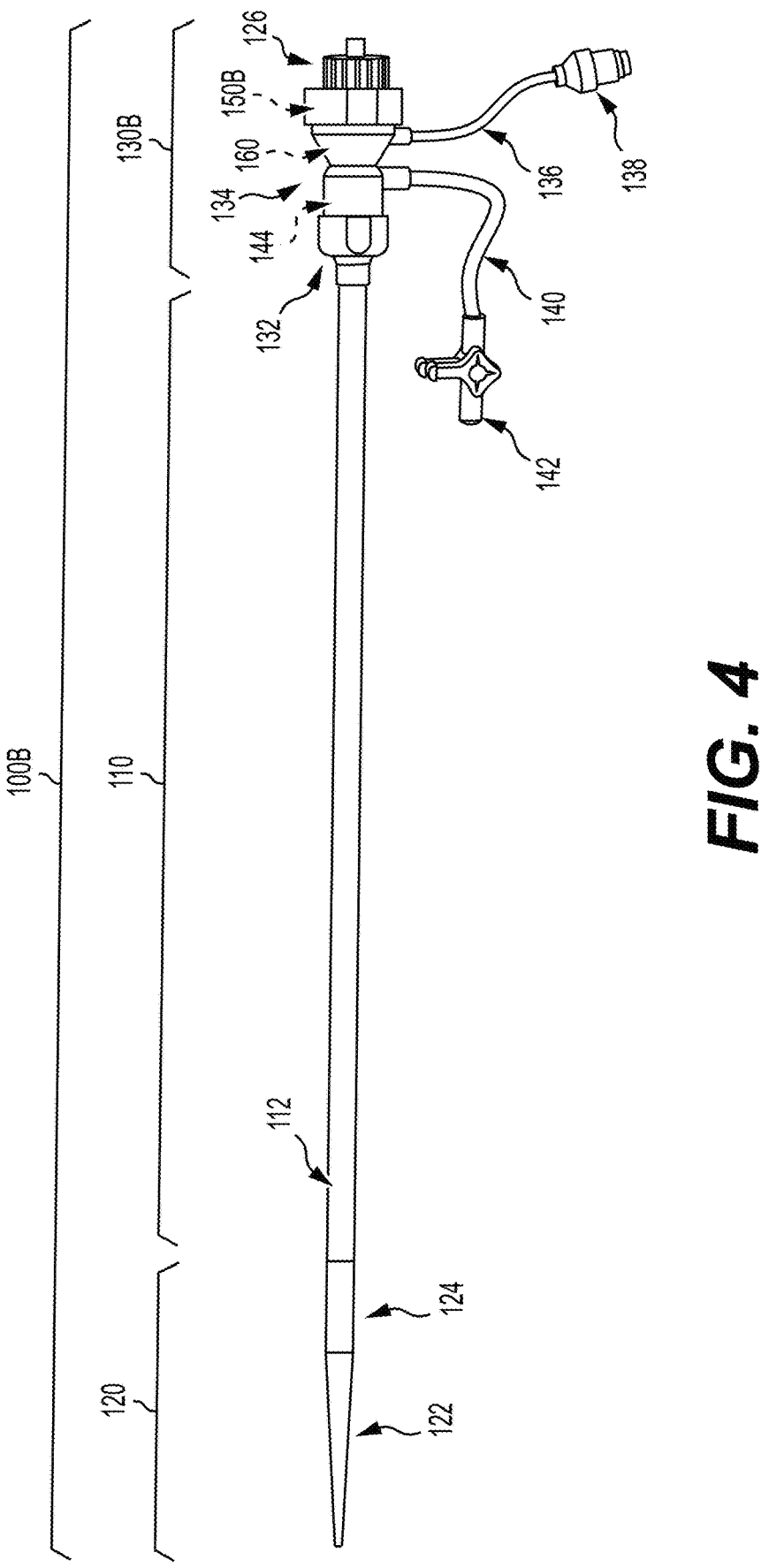
FIG. 4 is a perspective assembly view of an introducer sheath system according to another embodiment of the present disclosure.

With reference to FIG. 4, an assembly view of an alternative introducer sheath system 100B is shown. In general, the embodiment 100B illustrated in FIG. 4 may be the same as or similar to the embodiment illustrated in FIG. 1, except that the pressure regulator 150B is arranged coaxially, rather than offset. In this embodiment, as in the prior embodiment, the system 100A includes a sheath 110, a dilator 120 and a hub assembly 130B, wherein similar components are numbered the same, and the same or similar alternative features may be employed.

Figures 5A, 5B:
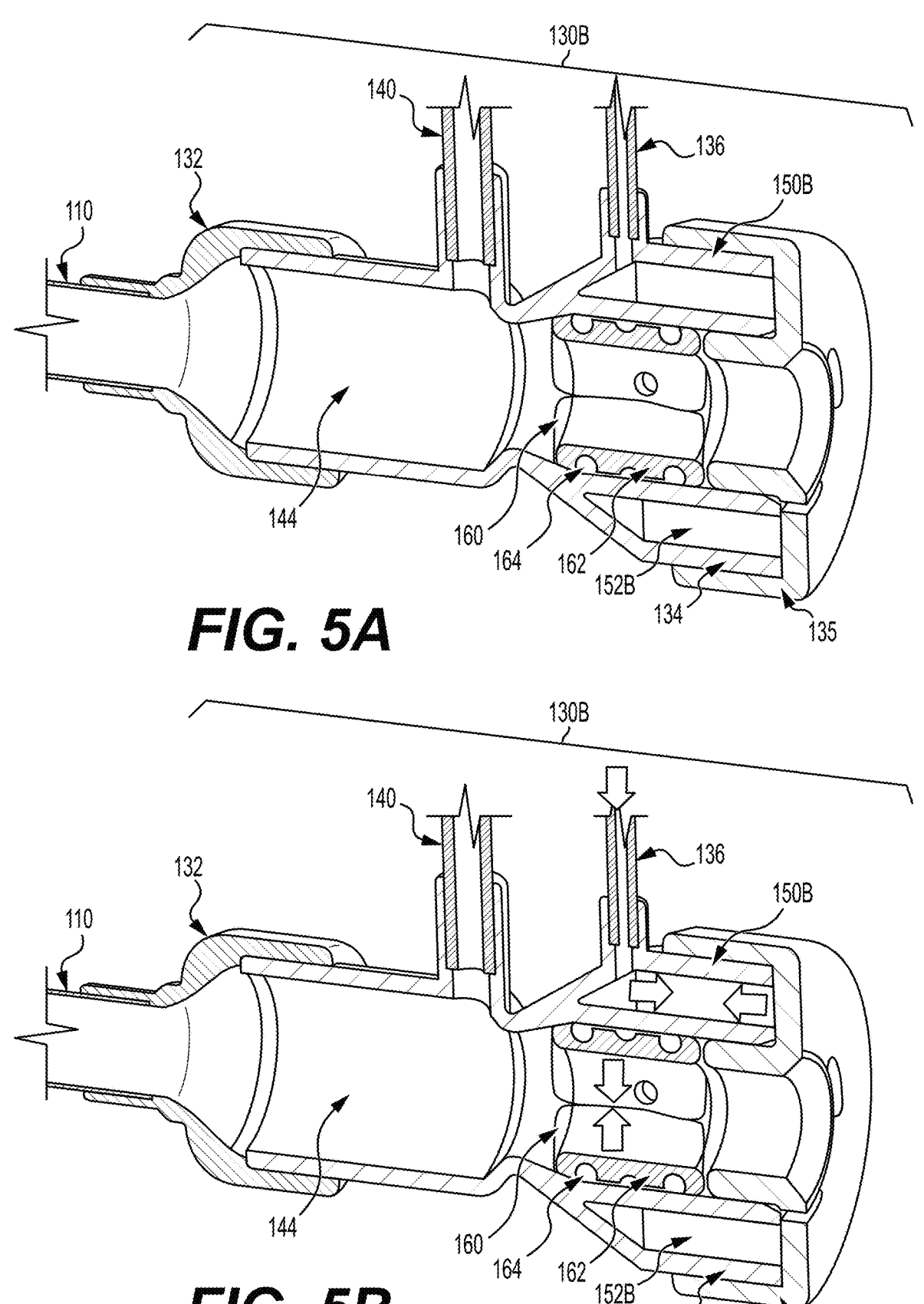
FIGS. 5A and 5B are longitudinal sectional views of the proximal portion of the introducer sheath system shown in FIG. 4.

Differences in the configuration of the pressure regulator 150B may be better appreciated with reference to FIGS. 5A and 5B, which are longitudinal cross-sectional views of the hub 130B. Again, similar components are numbered the same, and generally have the same or similar function, but the configuration if different. FIG. 5A shows the sleeve 160 of the hemostatic valve in an unpressurized state (as shipped), and FIG. 5B shows the sleeve 160 in a pressurized state (in use). With specific reference to FIG. 5B, liquid (e.g., saline) may be injected into the valve line 136 (as indicated by top block arrow) to pressurize the space between the valve body and the sleeve 160 causing it to collapse (as indicated by bottom block arrows). At the same time, the closed-cell foam member 152B is compressed (as indicated by middle block arrows), thus mitigating the increase of friction on devices inserted therethrough, as described previously. In the embodiment, the closed-cell foam member 152B may be in the configuration of an annular disc or tube, as shown.

Figure 6A:
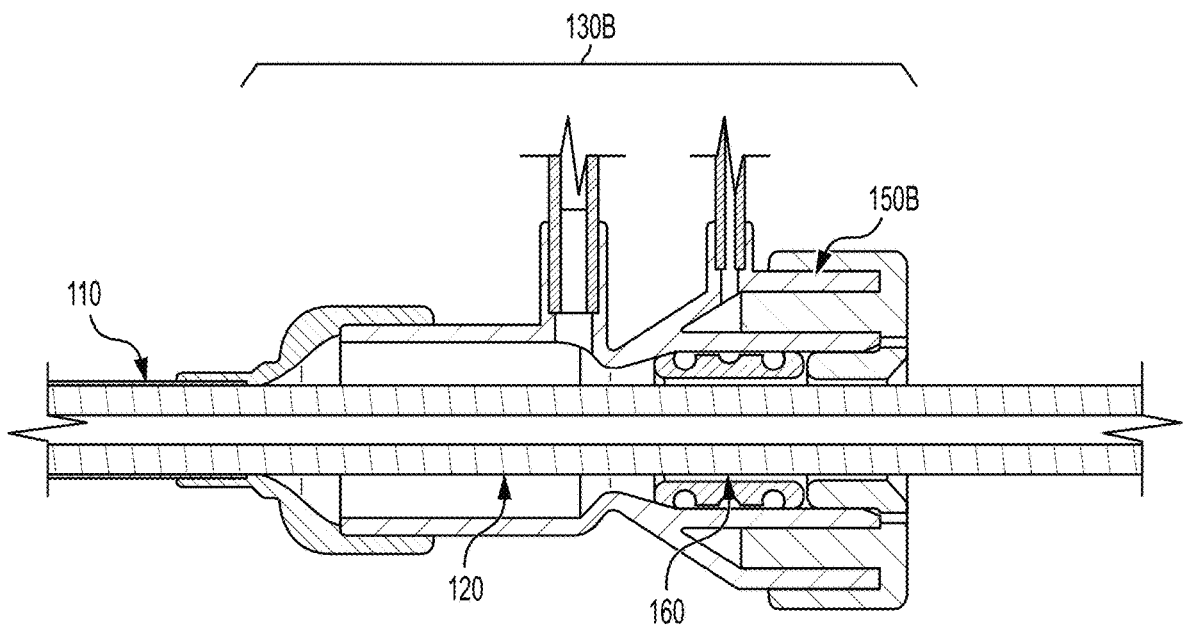
FIGS. 6A and 6B are longitudinal sectional views of the proximal portion of the introducer sheath system shown in FIG. 4 showing a dilator inserted and withdrawn, respectively.
Figure 6B:
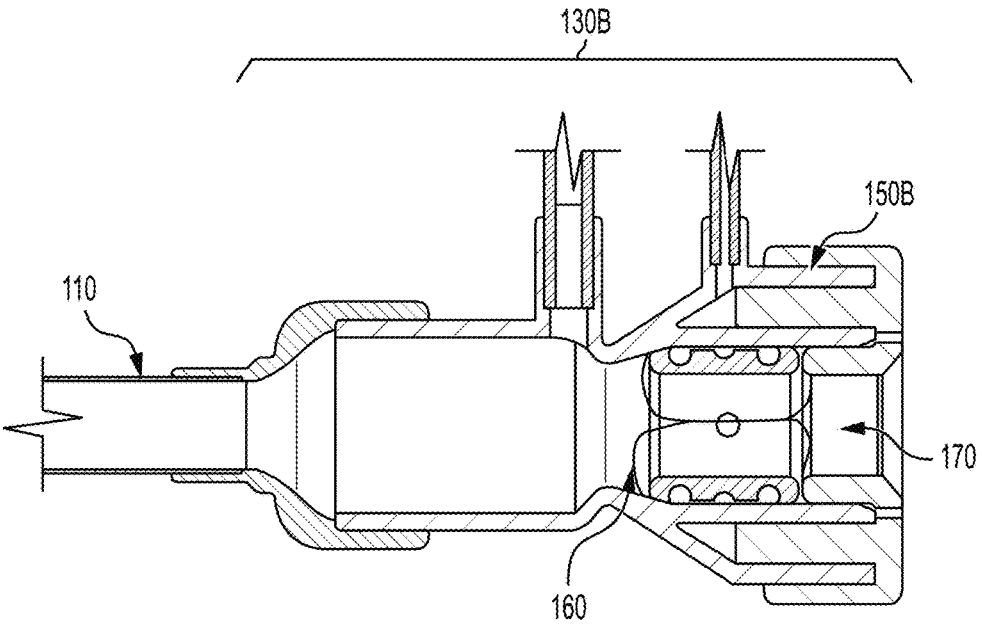

FIGS. 6A and 6B are longitudinal cross-sectional views focusing on the effect on the hemostatic valve with the dilator 120 inserted (FIG. 5A) and the dilator 120 removed (FIG. 5B). When pressurized, the sleeve 160 of the hemostatic valve is collapsed, as shown in FIG. 5B, to prevent back bleeding when no device is inserted therein. When the dilator 120 is inserted through the on-axis port 170, as shown in FIG. 5A, the sleeve 160 of the hemostatic valve expands to accommodate the dilator 120 while maintaining a seal around the dilator 120 to prevent back bleeding. The same is true when one or more other devices are inserted into the valve via on-axis port 170: the sleeve expands, pressure increases, and a hemostatic seal is maintained. By virtue of the pressure regulator 150B, the increase in pressure is mitigated and thus the additional friction on devices inserted therein is also mitigated.

Figure 7A:
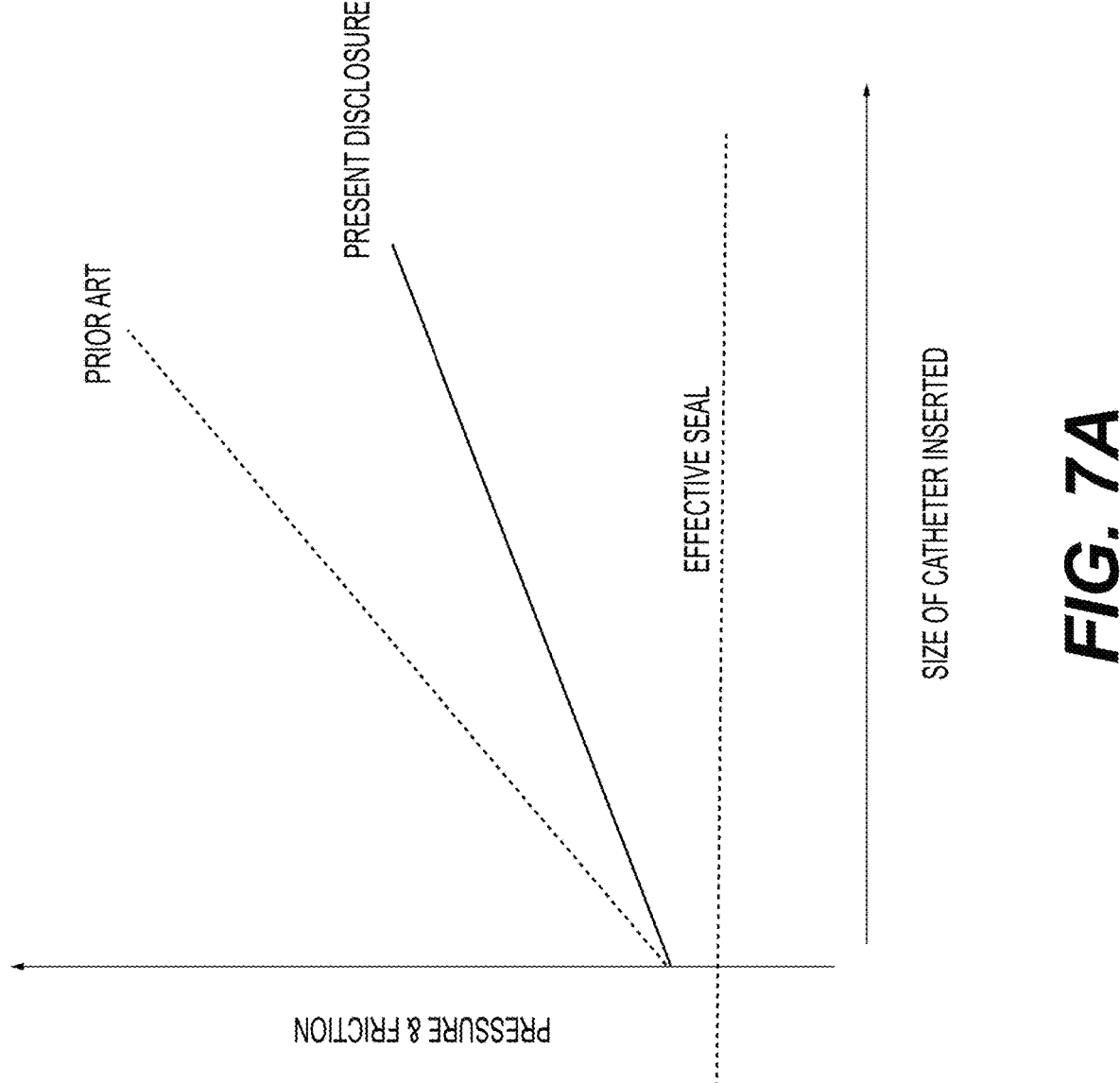
FIG. 7A is a composite graph of pressure and friction vs. size (diameter) of devices inserted into a hemostatic valve.

This relationship is schematically shown in FIG. 7A, which shows a composite graph of pressure and friction vs. size (diameter) of devices inserted into the valve. In general, the slope of both the pressure vs. size and friction vs. size is greater with prior art devices. With the pressure regulator 150 of the present invention, the curve is flatter, i.e., the slope is less than the prior art. As the size of the inserted device increases, the increase in pressure and friction is mitigated by the pressure regulator 150 as compared to the prior art. In the case of pressure vs. size, the slope may be characterized as the inverse of compliance, wherein the pressure regulator 150A of the present disclosure provides greater compliance than the prior art.

Figures 7B, 7C:
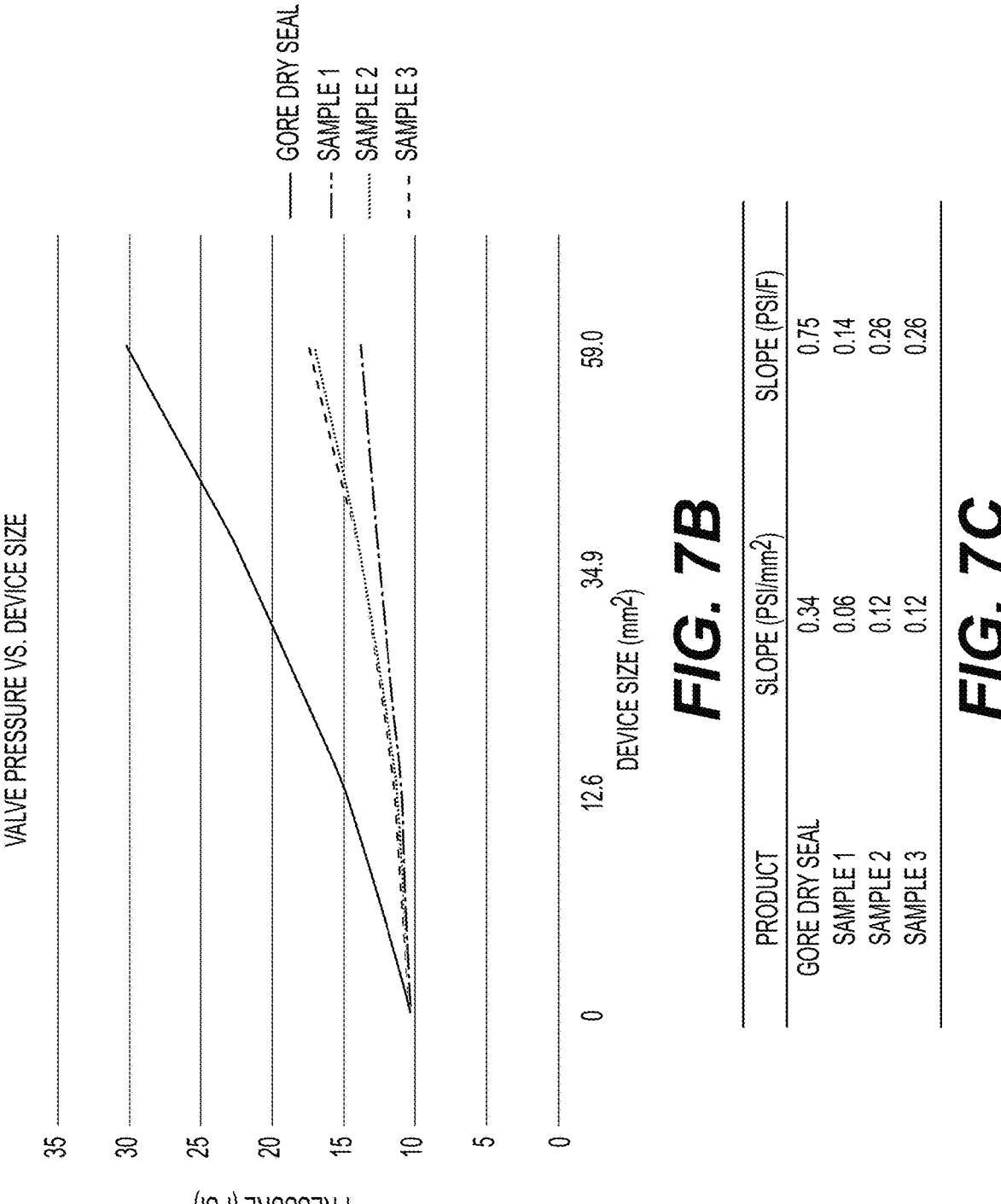
FIG. 7B is a line graph showing test data of valve pressure (PSI) vs. device size ($mm^2$).
FIG. 7C is a table of the slope of each data series from FIG. 7B taken along a best-fit line.

In FIG. 7B, which shows a line graph of valve pressure (PSI) vs. device size (mm²), this distinction becomes more evident. In this test, a 26 F prior art device (Gore® Dry Seal Flex Introducer Sheath) was compared to three samples of 26 F introducer sheath systems built according to the embodiment illustrated in FIG. 1. With each test run, the hemostatic valve was pressurized with saline to 10 PSI, and dilators of 12 F, 20 F and 26 F were sequentially inserted into the hemostatic valve. Pressure measurements in the valve chamber were taken with no dilator in place and with each of the different sized dilators in place. In all instances, the pressure increased as larger devices were inserted. However, the rate of increase was much lower with the samples built according to the present disclosure as compared to the prior art.

As shown in FIG. 7C, which is a table of the slope of each data series from FIG. 7B taken along a best-fit line. The prior art device has a slope of 0.34 PSI/mm² on a device area basis, or 0.75 PSI/F on a device diameter basis. (Note that F is an abbreviation for French, a standard metric in the catheter art, which is equal to 3 mm.) By comparison, the samples of devices built according to the present disclosure had a slope less than half of the prior art device. Again, lower pressure values correspond to lower friction for devices inserted into the valve.

By way of example, not necessarily limitation, the pressure regulator of the present disclosure may mitigate pressure increases with device size increases (in terms of device area) at a rate of less than 0.30 PSI/mm², preferably less than 0.20 PSI/mm², and more preferably less than 0.15 PSI/mm². Also, by way of example, not necessarily limitation, the pressure regulator of the present disclosure may mitigate pressure increases with device size increases (in terms of device diameter) at a rate of less than 0.70 PSI/F, preferably less than 0.50 PSI/F, and more preferably less than 0.35 PSI/F.

Figure 8A:
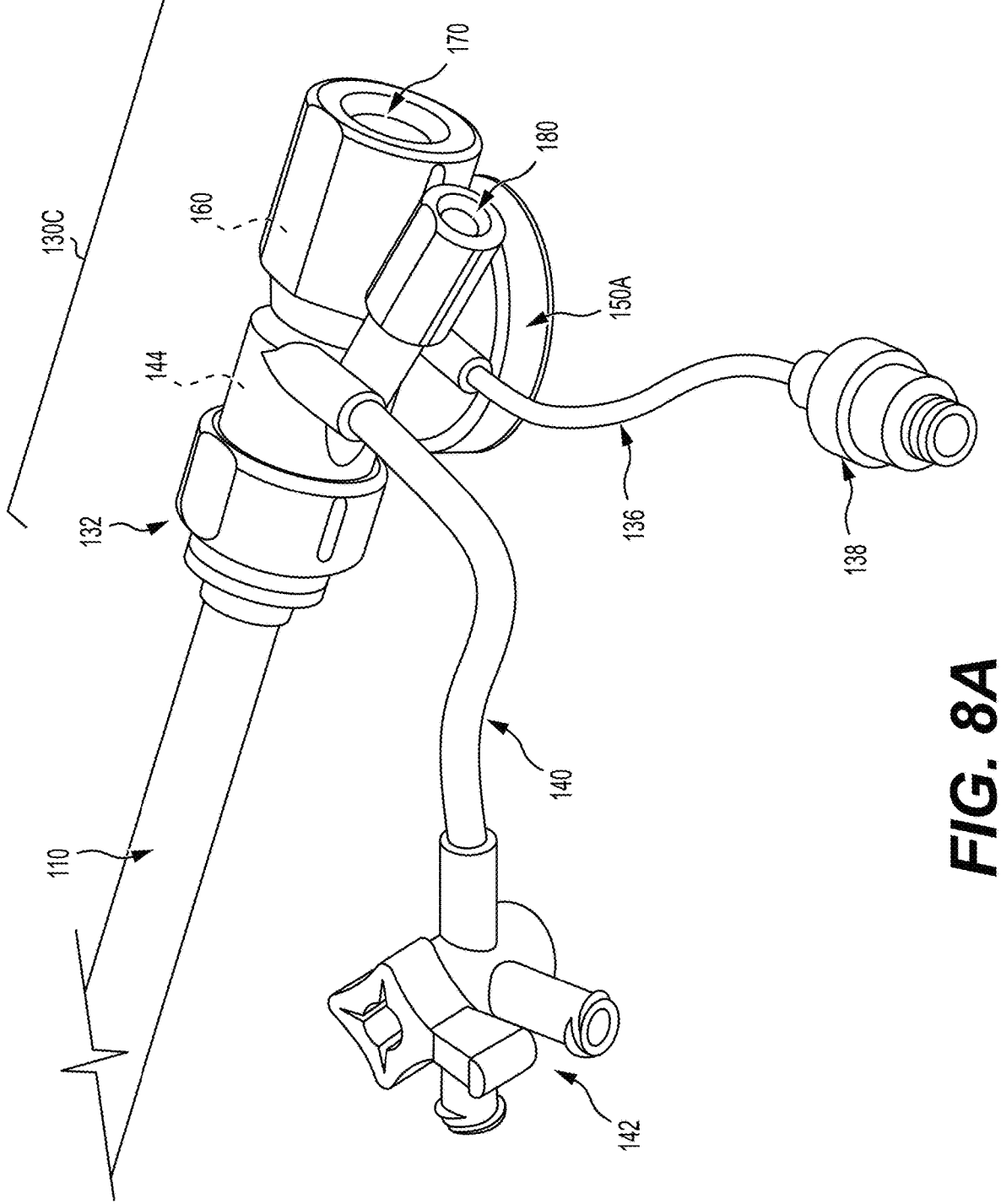
FIGS. 8A and 8B are perspective and longitudinal cross-sectional views, respectively, of a hub assembly according to an alternative embodiment of the present disclosure.

With reference to FIG. 8A, a perspective view of an alternative hub assembly 130C is shown. In general, the embodiment illustrated in FIG. 8A may be the same as or similar to the embodiment illustrated in FIG. 1, except that the hub assembly 130C includes an off-axis port 180 in addition to the on-axis port 170 as shown and described previously, thus comprising a dual valve hub 130C. In this embodiment, as in the prior embodiment, the hub 130C may be connected to a sheath 110 and used with a dilator 120 (not shown), wherein similar components are numbered the same, and the same or similar alternative features may be employed. In this example, the on-axis port 170 may be sized for large bore devices (e.g., >12 F) and the off-axis port 180 may be sized for normal bore devices (e.g., <12 F).

Figure 8B:
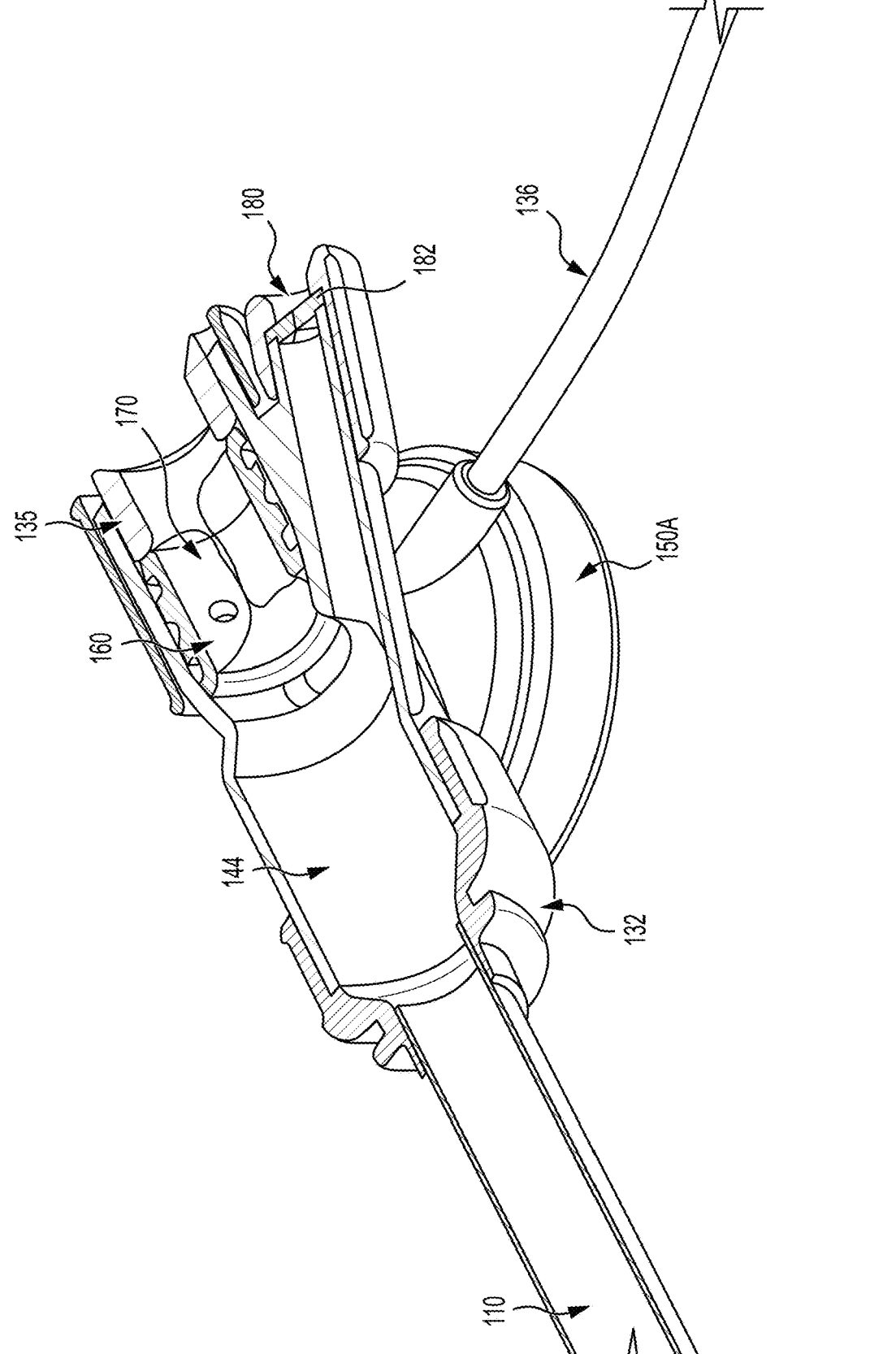

In general, providing an off-axis port 180 allows ancillary devices such as guidewires, diagnostic catheters, etc. to be introduced via the same introducer sheath system without requiring an additional vascular access site with the associated puncture and closure issues. As seen in FIG. 8B, the off-axis port 182 may include a separate hemostatic valve 182, which may comprise a passive seal (e.g., a slit elastomeric gasket) as shown, or an active seal like valve 160.

As a further alternative, either the on-axis port 170 or the off-axis port 180 may be configured for connection to an ECMO machine, with the typical connector configured for connection to ECMO tubing, thus providing one conduit for receiving oxygenated blood flow and the another conduit for receiving an interventional device.

Figure 9A:
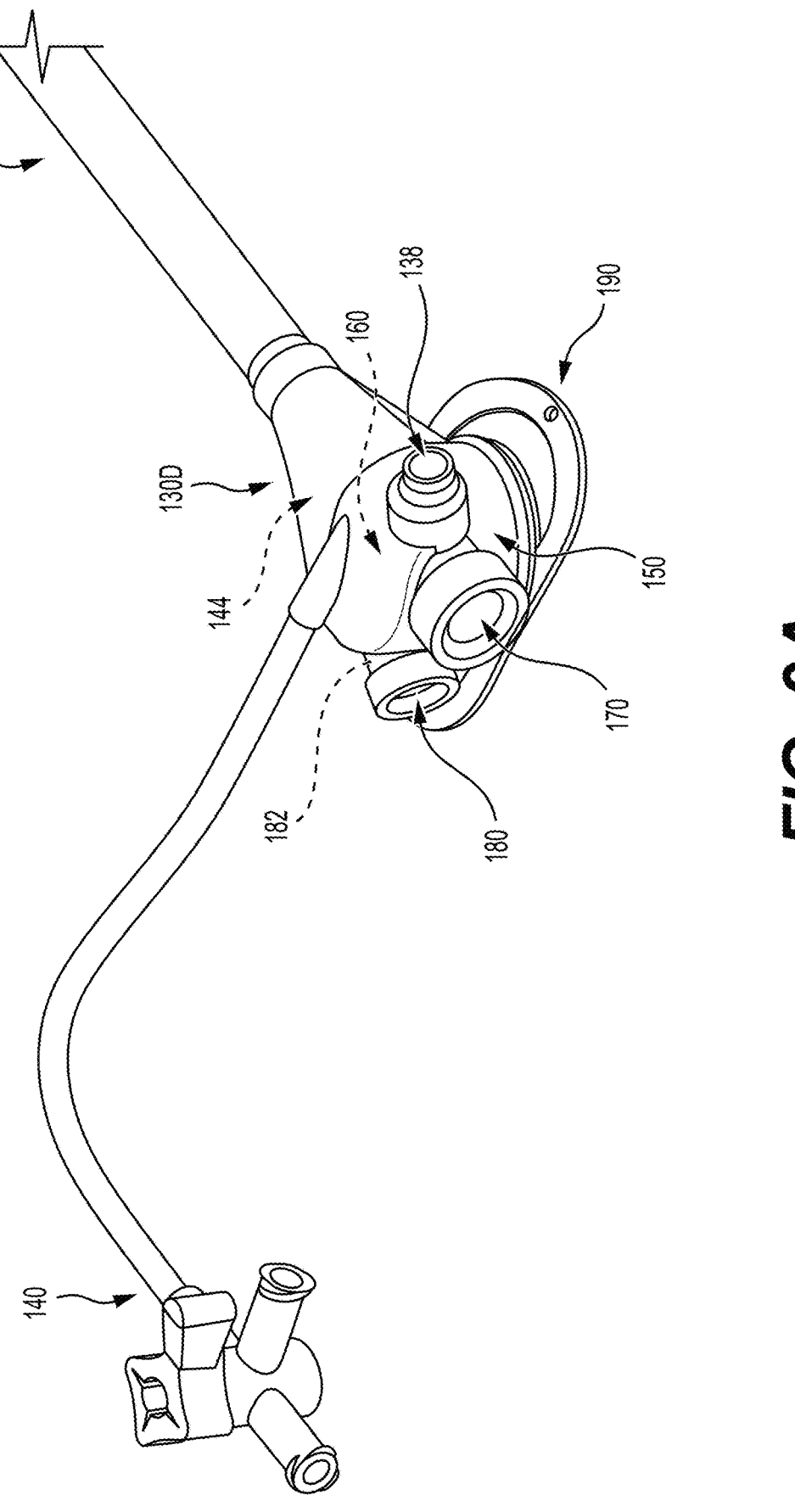
FIGS. 9A and 9B are perspective views of an anchor mechanism according to an embodiment of the present disclosure.
Figure 9B:
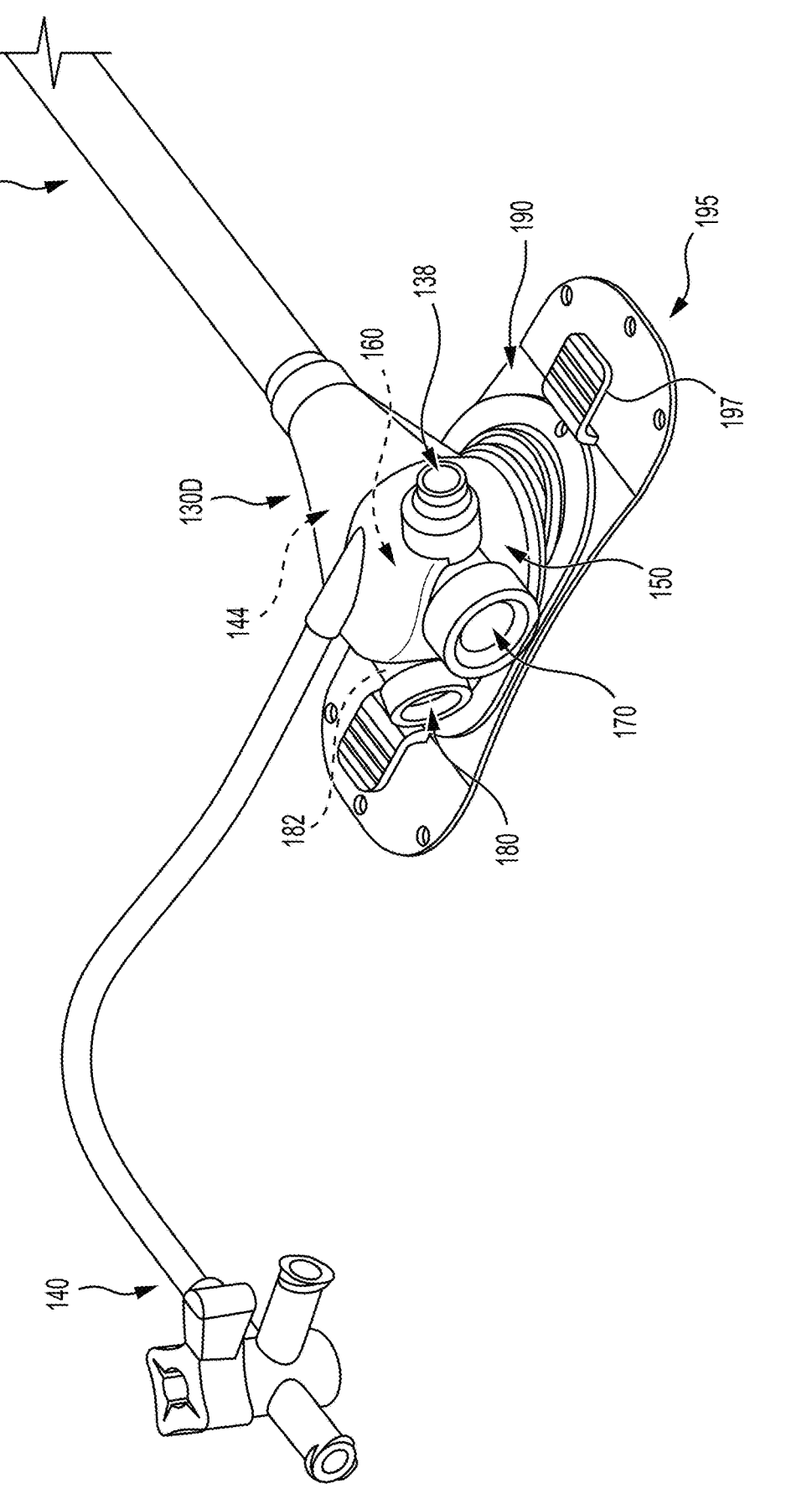

With references to FIGS. 9A and 9B, an alternative dual valve hub 130D is shown in perspective views. Dual valve hub 130D may have a different shape and form factor compared to hub 130C, but the active 160 and passive 182 hemostatic valves associated with each of the on-axis port 170 and off-axis port 180, respectively, may operate on the same or similar principles. In this embodiment, a couple of alternative design features are shown, which may be used in any of the hub assemblies 130 described herein. For example, to facilitate pressurization of the valve 160, the valve line 136 has been omitted in favor of a connector 138 (e.g., needleless valve) mounted directly to the housing. Additionally, anchor wings 190 are provided, which may be fixedly or releasably mounted to the base of the hub 130D. Anchor wings 190 enable the hub 130D to be anchored relative to the vascular access site by multiple means, such as by a surgical clamp placed on the wings 190 and drape and/or sutures placed through suture holes in the wings 190 and tied to the patient's skin or surgical dressing.

Additionally, as best seen in FIG. 9B, a secondary anchor member 195 may be releasably connected to the anchor wings 190 by snap-fit or the like. The secondary anchor member 195 may include an adhesive patch on the underside thereof for temporary adhesion to the patient's skin, surgical drape or dressing. Push-tabs 197 may be provided to release the secondary anchor member 195 from the anchor wings 190, and reattachment may be accomplished with a snap-fit by pressing the anchor wings 190 into the secondary anchor member 195. This releasable attachment means may allow for the introducer sheath to be released for manipulation and resecured once complete.

Generally, the remaining figures illustrate various alternative embodiments of select portions, elements or features of the introducer sheath systems described above. Although not illustrated as full systems, they may be incorporated into such systems individually or in various combinations.

Figures 10A, 10B, 10C, 10D, 10E:
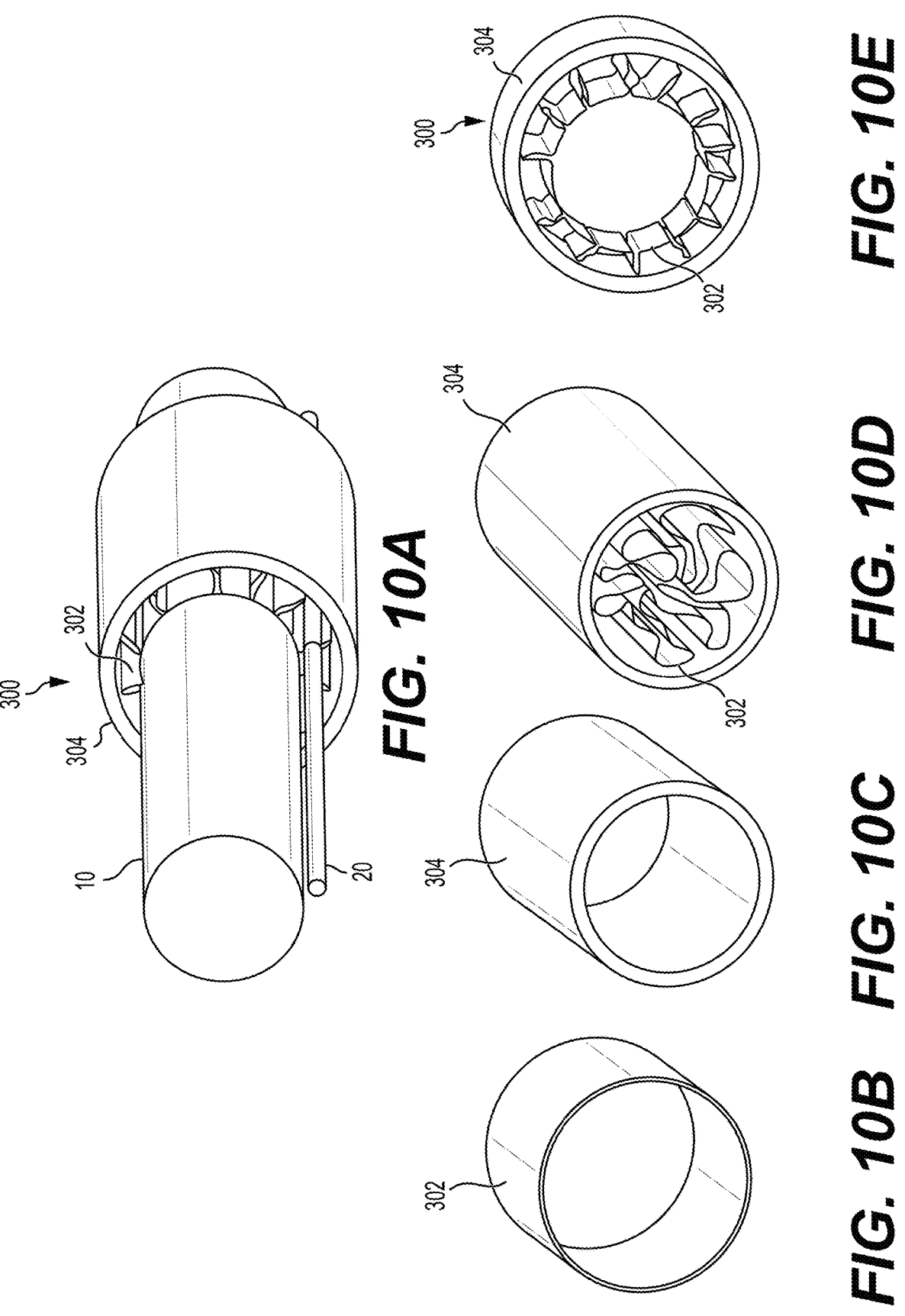
FIGS. 10A-10E are schematic perspective views of a hemostatic valve according to an alternative embodiment of the present disclosure.

In FIG. 10A, an alternative hemostatic valve 300 configuration is shown schematically in perspective view. In this embodiment, an inner sealing membrane 302 is provided in an outer tube or housing 304, wherein the sealing membrane has a larger circumferential length than the total contact perimeter of the devices (e.g., catheter 10 and/or guidewire 20) to be sealed upon. The inner sealing membrane 302 may be a thin walled elastomeric or non-elastomeric tube as shown in FIG. 10B, having a perimeter X and a thickness Y. The outer housing 304 may be a more rigid elastomeric or non-elastomeric tube as shown in FIG. 10C, having a perimeter <X and a thickness >Y. The inner member 302 may be folded or otherwise compacted to into outer member 304 as shown in FIG. 10D, with either end of the inner member 302 seal to the outer member 304 (not shown). When the space between the inner member 302 and the outer member 304 is pressurized, the inner member 302 seals around a plurality of of devices and device configurations inserted therethrough.

Figure 11:
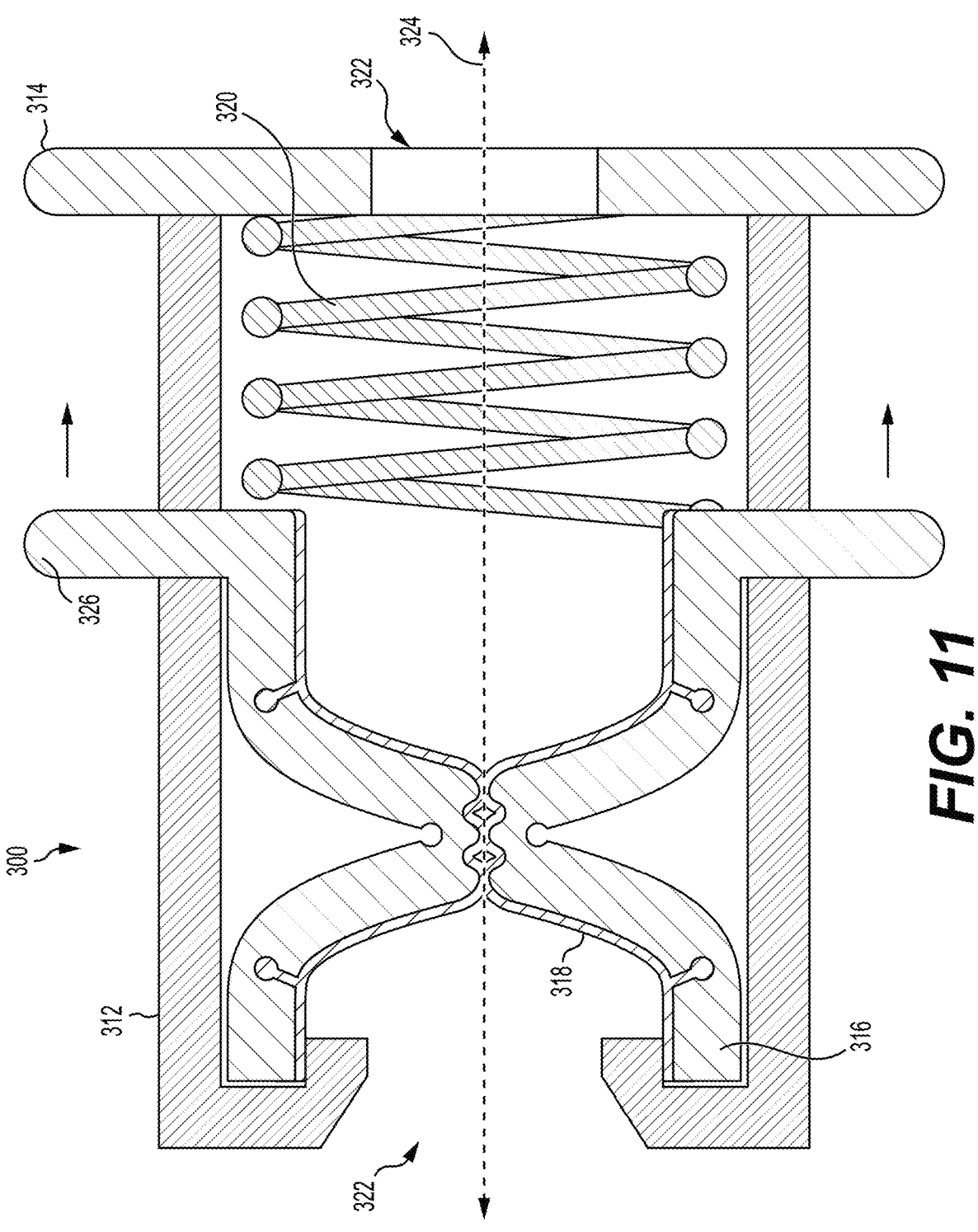
FIG. 11 is a schematic longitudinal cross-sectional view of a hemostatic valve according to another alternative embodiment of the present disclosure.

In FIG. 11, another alternative hemostatic valve 310 configuration is shown schematically in longitudinal cross-section. Valve 310 includes a fixed housing 312 in the shape of a hollow cylinder with finger grips 314 and openings 322 at either end. Within housing 312, an articulating member 316 is provided, which may comprise a compliant body over molded onto rigid articulating substrate. Articulating member 316 may include sealing rings at its inner surface to help increase sealing pressure by reducing contact surface. The articulating member 316 may be molded flat and then folded into the configuration shown. A membrane 318 may be provided on the inner surface of the articulating member 316, and the membrane 318 may comprise a permeable or non-permeable lubricious material such as ePTFE or sintered ePTFE. Also contained in housing 312 is a biasing member 320 that may comprise a spring, for example. Finger tabs 326 on the articulating member 316 may be compressed relative to finger tabs 314 on the housing 312 to open the articulating member 316, compress the spring 320 and allow passage of a device along axis 324. When a device is thus inserted through the openings 322 along axis 324, the spring 320 maintains a bias against the articulating member 316 to provide a hemostatic seal around such device. Thus, in this embodiment, the pressure to form a hemostatic seal is an active mechanism, as opposed to a hydraulic pressure as in prior embodiments.

Figure 12B:
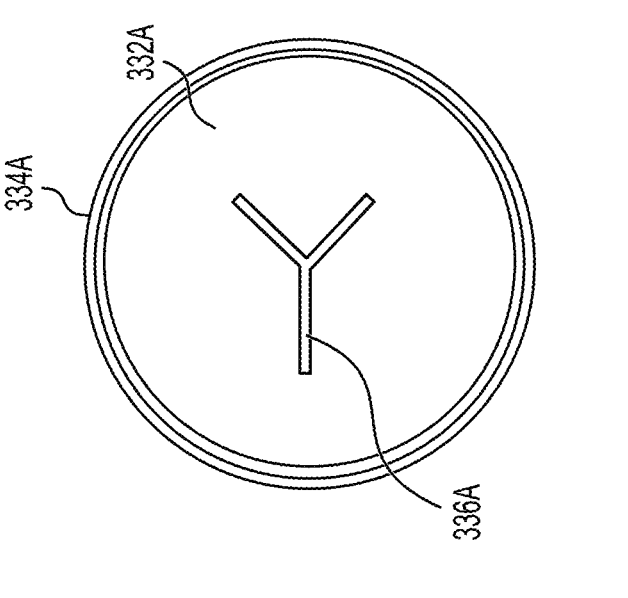
FIGS. 12A and 12B are schematic side and end views, respectively, of a hemostatic valve according to yet another alternative embodiment of the present disclosure.
Figure 12A:
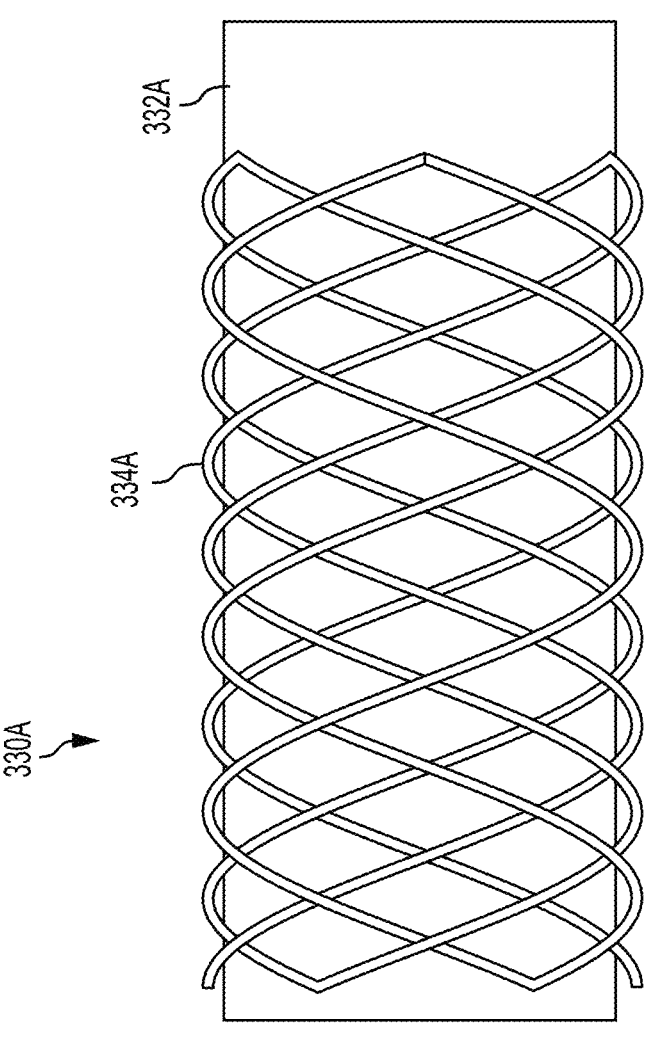

In FIGS. 12A and 12B, yet another alternative hemostatic valve 330A configuration is shown schematically in side and end views, respectively. With reference to FIG. 12A, a compressible inner member 332A is disposed in an outer structure 334A. The inner member 332A may comprise a compressible or compliant material such as a foam or a soft elastomer in the form of a cylinder or membrane, including, as best seen in FIG. 12B, a pre-formed slit 336A or lumen with a greater length than the circumference of a device to be passed therethrough. The outer structure 334A may comprise a wire braid formed of an elastic metal, a super elastic metal or a shape memory metal such as nitinol. The outer structure 334A may provide an elastic compressive force on the inner member 332A that can be overcome by inserting a device through compressible inner member 332A to thereby provide a hemostatic seal. Thus, in this embodiment, the pressure to form a hemostatic seal is a passive mechanism, as opposed to a hydraulic pressure or active mechanism as in prior embodiments.

Figures 12C, 12D, 12E:
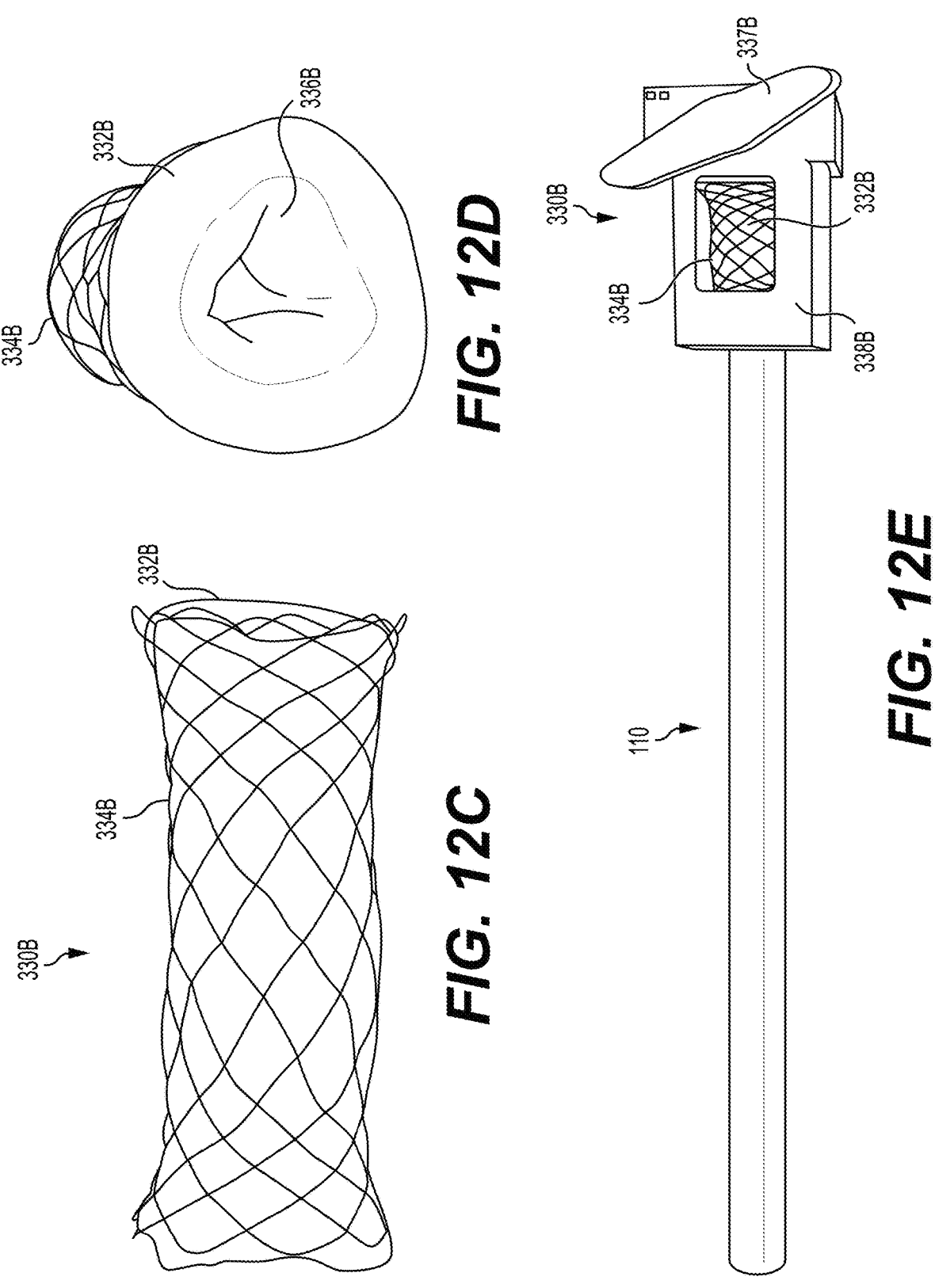
FIGS. 12C, 12D, and 12E are schematic side, end and plan views, respectively, of a hemostatic valve according to a further alternative embodiment of the present disclosure.

In FIGS. 12C, 12D and 12E, a variation of the hemostatic valve 330A is shown schematically in side, end and perspective views, respectively. In this embodiment, hemostatic valve 330B includes a tubular outer structure 334B such as a wire braid that collapses diametrically when elongated. An inner member 332B is disposed in the outer structure 334B and includes an opening 336B. The inner member 332B, including opening 336B, may comprise the same or similar structure and material as inner member 332A and opening 336A described previously. The outer structure 334B and inner member 332B may be disposed in a housing 338B connected to a sheath 110 as best seen in FIG. 12E. An actuation member 337B may be rotationally mounted to the housing 338B and operably coupled to the outer member 334B to cause it to shorten or lengthen. By actuating the lever 337B and lengthening the outer member 334B, the inner member 332B tends to collapse and close the lumen 336B, thereby creating a hemostatic seal about a device inserted therein. The lever 337B may be actuated in the opposite direction to shorten the outer member 334B, thus opening the lumen 336B and allowing the inserted device to move freely therein. Thus, in this embodiment, the pressure to form a hemostatic seal is an active mechanism actuated by elongation.

Figures 12F, 12G:
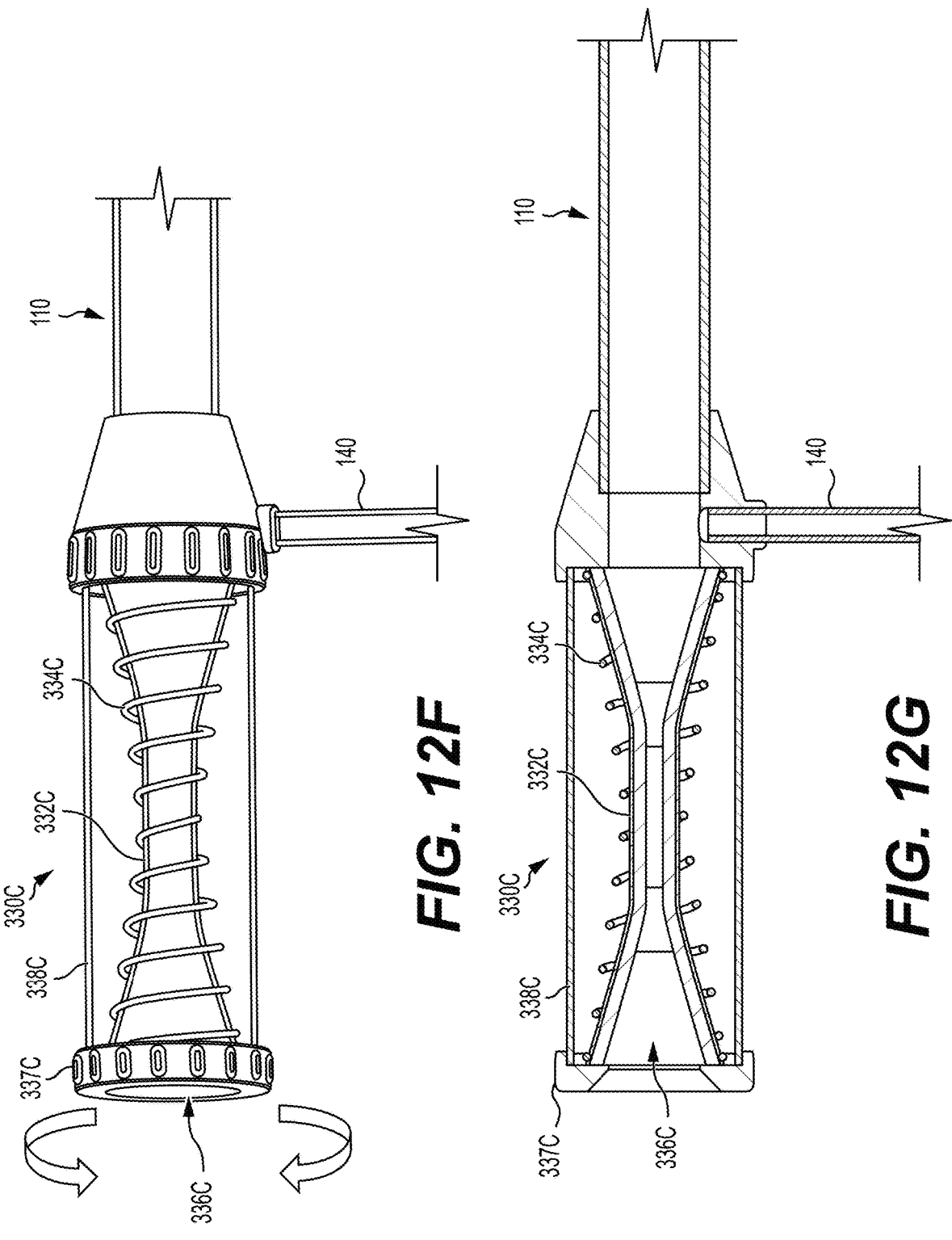
FIGS. 12F and 12G are side and longitudinal cross-sectional views, respectively, of a hemostatic valve according to yet a further alternative embodiment of the present disclosure.

In FIGS. 12F and 12G, a variation of the hemostatic valve 330B is shown schematically in side and longitudinal cross-sectional views, respectively. In this embodiment, hemostatic valve 330C includes a tubular outer structure 334C such as a wire coil that collapses diametrically when rotated. An inner member 332C is disposed in the outer structure 334C and includes an opening 336C. The inner member 332C, including opening 336C, may comprise the same or similar structure and material as inner member 332A and opening 336A described previously. The outer structure 334C and inner member 332C may be disposed in a housing 338C connected to a sheath 110. An actuation member 337C may be rotationally mounted to the housing 338C and operably coupled to the outer member 334C to cause it to diametrically open or close by rotation. By rotating the actuation member 337C in one direction, the inner member 332C tends to diametrically collapse and close the lumen 336C, thereby creating a hemostatic seal about a device inserted therein. When the actuation member 337C may be rotated in the opposite direction, the inner member tends to diametrically expand, thus opening the lumen 336C and allowing the inserted device to move freely therein. Thus, in this embodiment, the pressure to form a hemostatic seal is an active mechanism actuated by rotation.

Figures 13A, 13B, 13C, 13D:
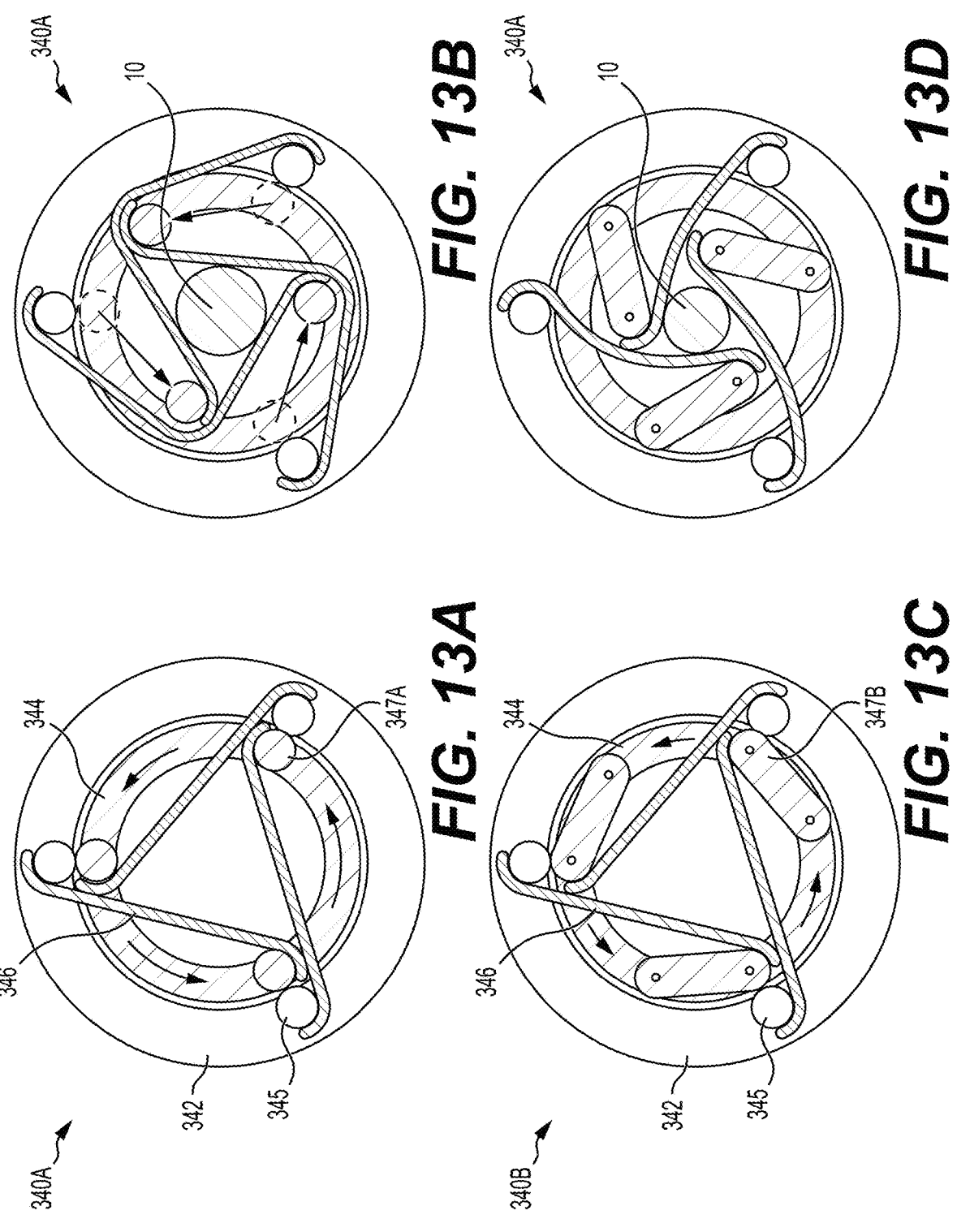
FIGS. 13A, 13B, 13C, and 13D are schematic transverse cross-sectional views of a hemostatic valve according to another alternative embodiment of the present disclosure.

FIGS. 13A-13D, show, in cross section, alternative hemostatic valves 340A and 340B which are also activated by rotation. FIGS. 13A and 13B show a 2-point strap valve 340A in open and closed positions, respectively. Valve 340A may include a relatively fixed outer body 342 and a relatively rotational inner body 344. A plurality of straps 346, in the form of an elastic or inelastic polymer film or membrane, may be connected at one end to the fixed outer body 342 by an anchor 345 such as a pin, and may be connected at the other end to the rotational inner body 344 by another anchor 347A such as a pin. In this example, three straps 346 are used and form a triangular opening in the center. Alternatively, more than three straps 346 may be used, and the resulting opening may have a different shape with more sides. When the inner body 344 is rotated in one direction (as indicated by the arrows) relative to the outer body 342, the anchor points 347A impinge on the straps 346 causing the triangular opening to cinched closed and seal around a device (e.g., catheter 10) as shown in FIG. 13B. When the inner body 344 is rotated in the other direction, the opening expands to release the device 10.

FIGS. 13C and 13D show a connecting arm strap valve 340B in open and closed positions, respectively. Valve 340B may be the same or similar to valve 340A except that valve 340B in this embodiment utilizes connecting arms 347B, rather than anchor points 347A, to connect the straps 346 to the inner body 344. This allows the straps 346 to attain a smaller cinched opening for sealing around a smaller device such as a guidewire 20 as shown in FIG. 13D. Otherwise, the operational principles are the same.

Yet another hemostatic valve 350 embodiment that utilizes an active rotational mechanism is shown schematically in FIG. 14, which is an end view. In this embodiment, the hemostatic valve 350 utilizes a plurality of iris leaflets 352 coupled to a rotating ring 354 at a plurality of pivot points. The ring 354 may be rotationally mounted in and to the housing 358. An inner tubular membrane 356 may be disposed in the aperture defined by the iris leaflets 352. When the ring 354 is rotated in one direction relative to the housing 358, the iris leaflets 352 close, thus compressing the inner tubular membrane 354 about an inserted device to form a hemostatic seal. When the ring 354 is rotated in the other direction relative to the housing 358, the iris leaflets 352 open to decompress the inner tubular membrane 354 and allow free movement of the inserted device.

With reference to FIGS. 15A and 15B, which are perspective and end views, respectively, yet another hemostatic valve 360 is shown schematically. This embodiment utilizes a singular tubular sleeve 362, similar to the sleeve 160 described with reference to FIG. 3, except that tubular sleeve 362 is twisted along its longitudinal axis. Twisted sleeve 362 may be made of an elastic or inelastic material, for example. As in prior embodiments, hydraulic pressure may be introduced between the relatively rigid outer housing 364 and the twisted sleeve 362 to cause it to collapse about a device inserted therein. To facilitate twisting of the sleeve 362, one end may be connected to the housing 364 and the other end may be connected to a ring 368. Once the sleeve 362 is mounted, the ring 368 may be rotated relative to the housing 364 to twist the sleeve 362, after which the ring 368 may be fixed to the housing 364 to maintain the twisted shape of the sleeve 362.

Figure 16A:
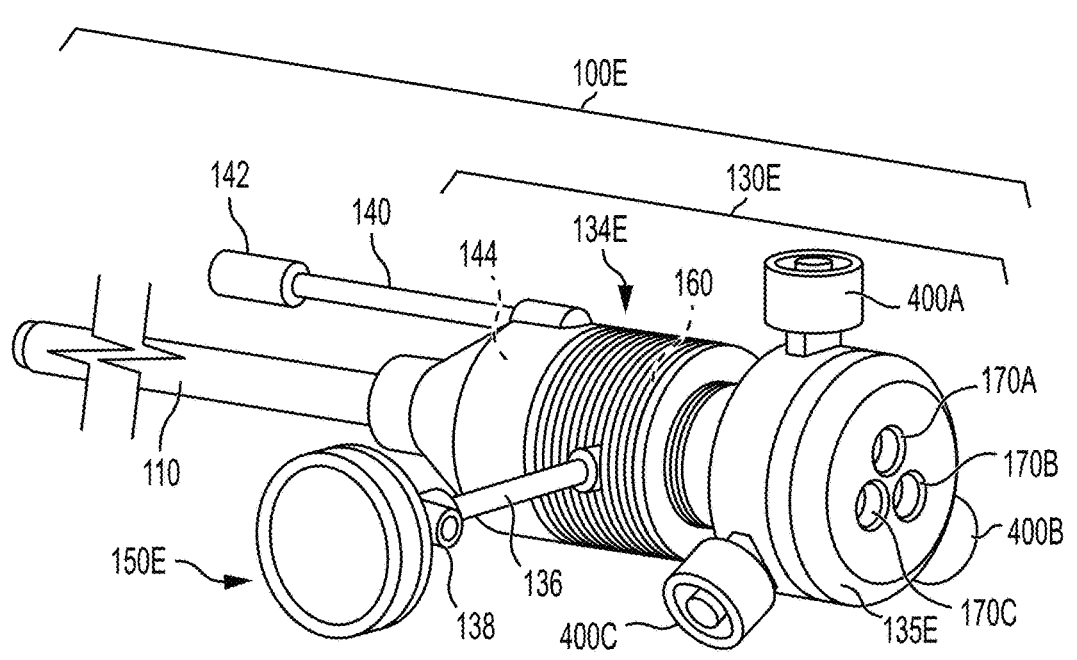
FIGS. 16A and 16B are perspective and longitudinal cross-sectional views, respectively, of an introducer sheath system according to a further embodiment of the present disclosure.
Figure 16B:
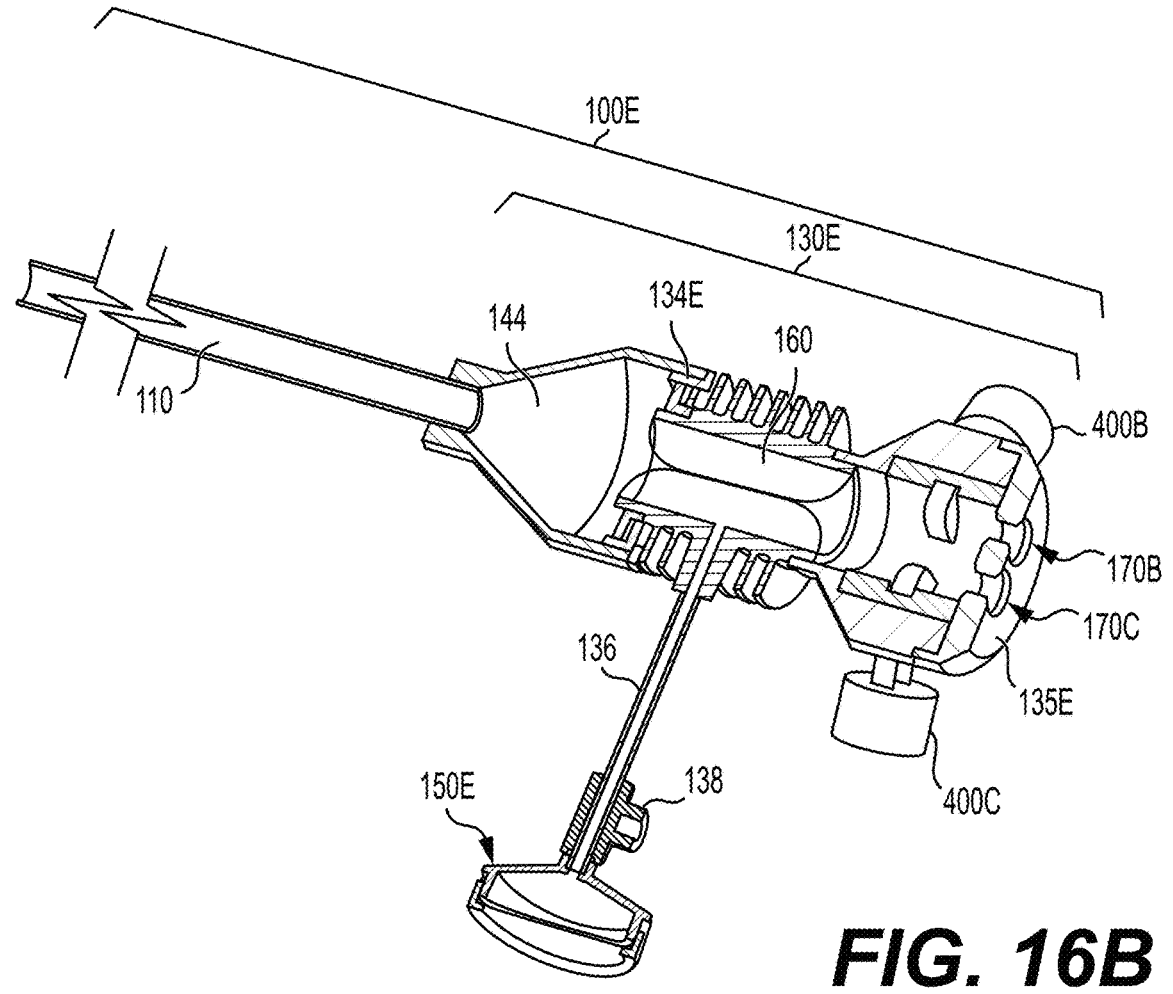

With reference to FIGS. 16A and 16B, an assembly view of an alternative introducer sheath system 100E is shown in perspective view and longitudinal cross-sectional view, respectively. In general, the embodiment 100E illustrated in FIGS. 16A and 16B may be the same as or similar to the embodiment illustrated in FIG. 1, with a few exceptions. In this embodiment, as in the prior embodiment, the system 100E includes a sheath 110, a dilator (not shown) and a hub assembly 130E, wherein similar components are numbered the same, and the same or similar alternative features may be employed.

In this embodiment, the pressure regulator 150E is arranged separate from the hub housing 134E and fluidly connected thereto via valve line 136, with associated connector 138 for pressurizing the hemostatic valve 160. As mentioned previously, the pressure regulator may be integral with the hub, connected to the hub via tubing, or completely apart from the hub as a separate component.

Also in this embodiment, a plurality of ports 170A, 170B and 170C are provided in housing cap 135E. Each of the ports 170A, 170B and 170C provide passage for an inserted device (not shown) into the common hemostatic valve 160, which is capable of sealing around multiple devices.

Further in the embodiment, brakes 400A, 400B and 400C are provided, in association with the ports 170A, 170B and 170C, respectively. The brakes 400A, 400B and 400C are configured to engage devices inserted into the ports 170A, 170B and 170C to limit longitudinal movement thereof and maintain their intravascular position. The brakes 400A, 400B and 400C may comprise push buttons that are biased in a normally braked position, wherein depression of a push button releases the brake and allows free movement of a device inserted therein.

Figure 17:
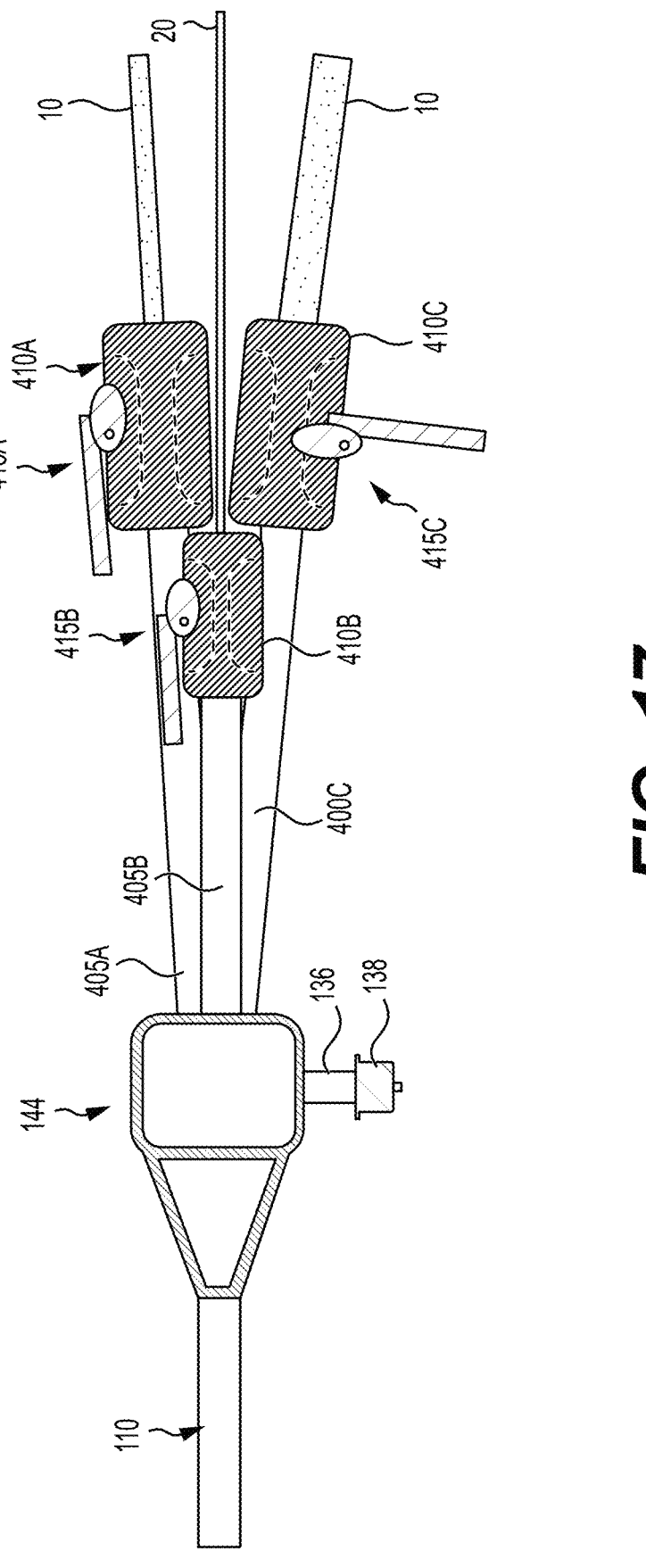
FIG. 17 is a schematic top view of a portion of an introducer sheath system according to a yet another embodiment of the present disclosure.
Figures 18A, 18B, 18C, 18D:
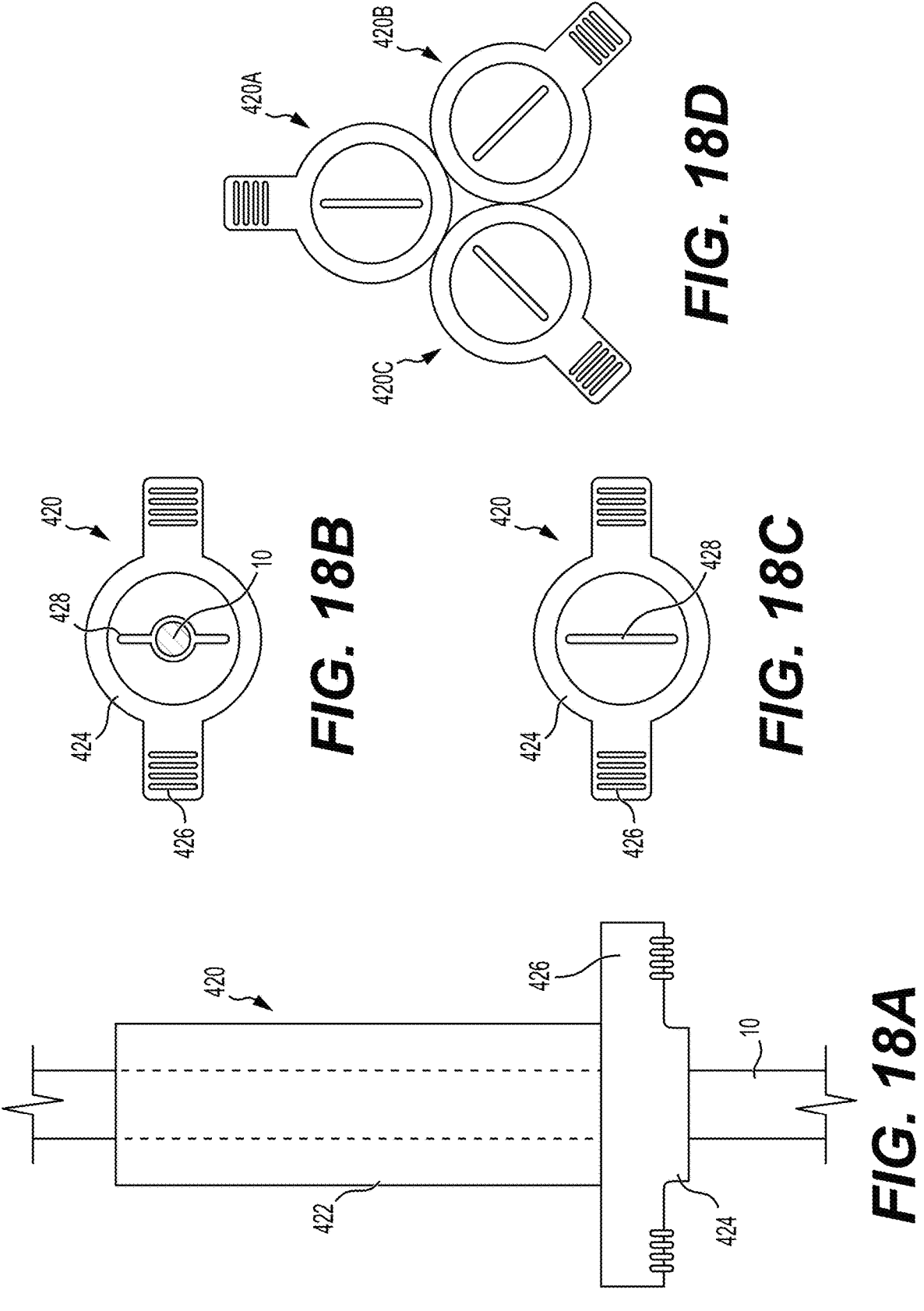
FIGS. 18A and 18B-18D are schematic side and end views of an isolation sheath according to an embodiment of the present disclosure.

With reference to FIG. 17, an alternative arrangement is shown schematically in a top view. Like the embodiment of FIGS. 16A and 16B, the embodiment of FIG. 17 provides a configuration to accommodate a plurality of inserted device such as catheters 10 and guidewires 20. However, rather than using a common hemostatic valve, a plurality of hemostatic valves 410A, 410B and 410C may be provided, connected to a common bubble capture chamber 144 by tubes 405A, 405B and 405C, respectively. The hemostatic valves 410A, 410B and 410C may comprise passive valves (e.g., slit gaskets) or active valves as described previously. Additionally, each hemostatic valve 410A, 410B and 410C may have an associated brake 415A, 415B and 415C, respectively. The brakes 415A, 415B and 415C may comprise push buttons as described previously, or cam levers as shown. Brakes 415A and 415B are shown in the open (unbraked) position, and brake 415C is shown in the closed (braked) position. As shown, each inserted device may have a dedicated hemostatic valve and brake, thus providing independent control of sealing and movement and avoiding potential device-to-device interaction or interference.

Another brake embodiment (not shown) may comprise one or two duck-bill gaskets disposed on either end of the sleeve 160 of the hemostatic valve. The duck-bill gaskets may be concave on one side and convex on the other. This configuration generally allows relatively free movement of devices inserted therein in the concave to convex direction, while resisting movement in the opposite direction. One gasket may be used to provide a uni-directional brake, for example to prevent back-out. Two gaskets may be used and arranged such that the convex sides are facing each other, or such that the concave sides are facing each other. In either case, the two gaskets arranged as such will resist movement of devices inserted therein in both directions, thus acting as a bi-directional brake.

An alternative embodiment for avoiding potential device-to-device interaction is illustrated in FIG. 18A-18D, which show side and ends views of an isolator sheath 420. Isolator sheath 420 may include a body portion 422, a cap 424 a slit or septum extending therethrough and finger tabs 426. The slit 428 may extend through the cap 424 and body 422 and may have a lubricious inner surface. The body 422 and cap may be formed of a compressible material (e.g., ePTFE) that is inherently lubricious to seal around an inserted device 10 while allowing relatively free longitudinal movement thereof. The isolator sheath 420 may be sized for insertion into any hemostatic valves described herein. The cap or flange 424 may be sized to prevent over-insertion. A plurality of isolator sheaths 420A, 420B and 420C may be used such that inserted devices are isolated from each other when placed in a common hemostatic valve.

Figures 19A, 19B, 19C:
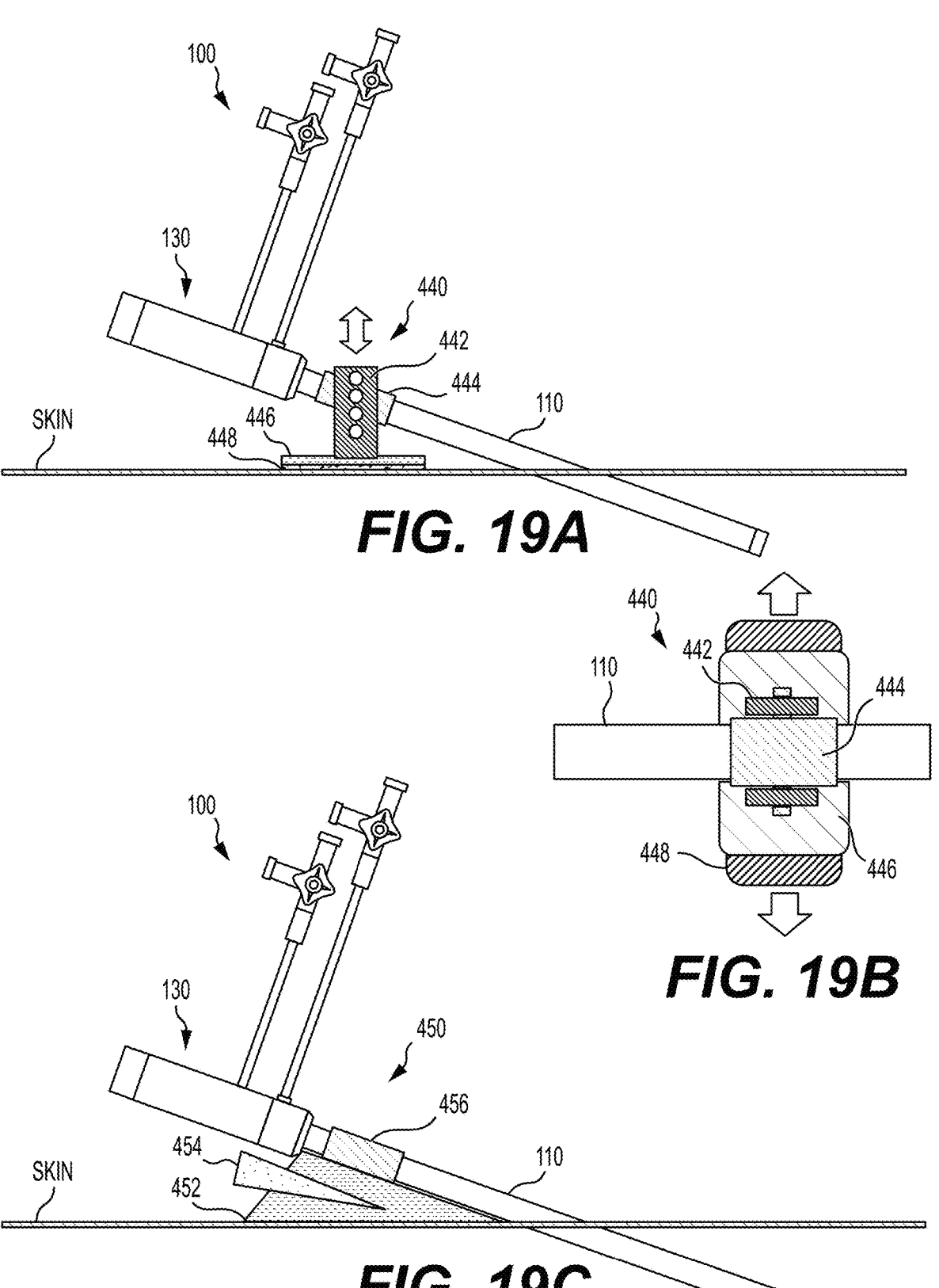
FIGS. 19A and 19B are schematic side and top views of an anchor mechanism according to an alternative embodiment of the present disclosure.
FIG. 19C is a schematic side view of an anchor mechanism according to another alternative embodiment of the present disclosure.

As previously described with reference to FIGS. 9A and 9B, the introducer sheath systems of the present disclosure may incorporate anchoring mechanisms to limit movement of the sheath once inserted into the vasculature, and specifically to mitigate back-out. The embodiments schematically illustrated in FIGS. 19A, 19B and 19C show alternative anchoring mechanisms that also accommodate different entry angles. Depending on the size of the patient and the depth of the blood vessel to be accessed, entry angles may vary.

FIG. 19A shows a side view and FIG. 19B shows a top view of an anchor mechanism 440 that is adjustable in height, specifically between the patient's skin and the sheath 110 adjacent the hub assembly 130. The anchor mechanism 440 may be integral to the system 100 or provided as a separate accessory device. Anchor mechanism 440 may include an adjustable and locking height stand 442, shown with holes that can be engaged to set the height and angle of the introducer sheath system 100. Those skilled in the art will recognize that other height adjustment embodiments may be employed. Anchor mechanism 440 may further include a pivoting body 444 that is clamped, adhesively joined, or otherwise connected to the sheath body 110. The anchor mechanism 440 may include a base plate 446 with an adhesive layer 448. Adhesive layer 448 may comprise a stretch-to-release adhesive as shown by block arrows in FIG. 19B for releasable or otherwise temporary attachment to the patient's skin, surgical dressing or the like.

FIG. 19C shows a side view another anchor mechanism 450 that is adjustable in height, specifically between the patient's skin and the sheath 110 adjacent the hub assembly 130. The anchor mechanism 450 may be integral to the system 100 or provided as a separate accessory device. Anchor mechanism 450 may include a primary wedge 452 and an angle adjustment wedge 454. The angle adjustment wedge 454 may be inserted into or withdrawn from the primary wedge 452 to adjust height and angle of the introducer sheath system 100. The primary wedge 452 may be secured to the sheath 110 proximate a distal aspect of the hub 130 by adhesive, Velcro® straps or other suitable connection. Each of the wedges 452 and 454 may comprise a rigid or compliant material such as foam. The primary wedge 452 may include a bottom adhesive layer releasable or otherwise temporary attachment to the patient's skin, surgical dressing or the like.

Dilator 120 may also incorporate alternative features, such as a cutting blade 480, as shown in FIGS. 20A, 20B and 20C to facilitate more predictable and improved results with suture-mediated closure as shown in FIGS. 20D, 20E and 20F. As seen in FIG. 20A, after access to the vasculature is achieved using a standard percutaneous access kit and placement of guidewire 20, the dilator 120 and sheath may be advanced toward the blood vessel over the guidewire 20 and through the skin and intervening subcutaneous tissue. A fixed or retractable blade 480 may be incorporated into the dilator distal of the constant diameter portion 124 in the tapered region 122 as seen in FIG. 20B. When positioned and optionally deployed, the blade may be used to cut a predictable incision into the blood vessel as shown in FIG. 20C. Cutting an incision, rather than simply dilating the vessel opening, may mitigate unpredictable tearing of the vessel wall and enable reliable closure. As seen in FIG. 20D, a plurality of sutures 490 may be deployed around the open incision using a suture-mediated closure device advanced over guidewire 20. The sutures 490 may be deployed either after or preferably before the incision is made, sometimes referred to as a pre-close operation. After the interventional procedure is complete and all devices are removed from the blood vessel, the incision may be closed by tightening the sutures 490 as shown in FIG. 20E. The sutures 490 may then be tied as shown in FIG. 20F using pledgets or knots.

All of the aspects described in the present disclosure (including references incorporated by reference, accompanying claims, abstract and drawings), may be combined in any order, in part or in full, or in any combination or modification, except when such are incompatible or inconsistent. Furthermore, each aspect may be replaced by alternative features serving the same, equivalent or similar purpose, unless expressly stated otherwise or inconsistent with the teachings herein. Thus, unless expressly stated otherwise, each aspect disclosed herein may be only an example of equivalent or similar features. It is intended that the invention be defined by the attached claims and their legal equivalents.

What is claimed is:

1. An introducer sheath system, comprising:
a tubular sheath;
a hub assembly connected to a proximal end of the tubular sheath;
a dilator extending through the hub assembly and the tubular sheath;
the hub assembly including a housing and a hemostatic valve disposed therein;
the hemostatic valve comprising a rigid valve body and a collapsible member, wherein the collapsible member closes when a space between the collapsible member and the rigid valve body is pressurized;
a pressure regulator connected to the hub assembly and in fluid communication with the space between the collapsible member and the rigid valve body; and
a sealed chamber including a closed-cell foam defined by the pressure regulator, the sealed chamber having an interior, wherein the interior of the sealed chamber is fluidly isolated from the space between the collapsible member and the rigid valve body.

2. The introducer sheath system as in claim 1, wherein the collapsible member is connected to the rigid valve body.

3. The introducer sheath system as in claim 1, wherein the space between the collapsible member and the rigid valve body is filled with a liquid.

4. The introducer sheath system as in claim 3, wherein the sealed chamber is filled with a gas.

5. The introducer sheath system as in claim 4, wherein the collapsible member comprises a sleeve.

6. The introducer sheath system as in claim 5, wherein the collapsible member comprises ePTFE.

7. The introducer sheath system as in claim 5, wherein the collapsible member comprises densified ePTFE.

8. The introducer sheath system as in claim 5, wherein the collapsible member comprises a laminate of FEP over ePTFE.

9. The introducer sheath system as in claim 5, wherein the collapsible member is inverted and wrapped around ends of the rigid valve body.

10. The introducer sheath system as in claim 1, wherein the pressure regulator mitigates a valve pressure increase as a function of a device size at a rate less than 0.70 PSI/F.

11. The introducer sheath system as in claim 1, wherein the pressure regulator mitigates a valve pressure increase as a function of a device size at a rate less than 0.50 PSI/F.

12. The introducer sheath system as in claim 1, wherein the pressure regulator mitigates a valve pressure increase as a function of a device size at a rate less than 0.35 PSI/F.

13. An introducer sheath system, comprising:
a tubular sheath;
a hub assembly connected to a proximal end of the tubular sheath, the hub assembly including a primary port and a secondary port;
a dilator extending through the primary port, the hub assembly and the tubular sheath;
the hub assembly including a housing and a hemostatic valve disposed therein;
the hemostatic valve comprising a rigid valve body and a collapsible member, wherein the collapsible member closes when a space between the collapsible member and the rigid valve body is pressurized;
a pressure regulator connected to the hub assembly and in fluid communication with the space between the collapsible member and the rigid valve body; and
a sealed chamber including a closed-cell foam defined by the pressure regulator, the sealed chamber having an interior, wherein the interior of the sealed chamber is fluidly isolated from the space between the collapsible member and the rigid valve body.

14. The introducer sheath system as in claim 13, wherein the housing of the hub assembly defines a bubble capture chamber with a vertical apex, and wherein a flush line is connected to the bubble capture chamber at the vertical apex to vent air bubbles from the bubble capture chamber.

15. The introducer sheath system as in claim 14, wherein the housing defining the bubble capture chamber is transparent to facilitate viewing bubbles in the bubble capture chamber.

16. The introducer sheath system as in claim 13, further comprising a brake connected to the housing of the hub assembly, wherein the brake is configured to engage a device inserted into at least one of the primary port and the secondary port.

17. The introducer sheath system as in claim 13, wherein the hub assembly includes a connector associated with one of the primary or secondary ports, wherein the connector is configured for connection to ECMO tubing for receiving oxygenated blood flow.

15

16

18. An introducer sheath, comprising:
a tubular sheath;
a hub assembly connected to a proximal end of the tubular sheath;
the hub assembly including a housing and a hemostatic valve disposed therein;
a pressure regulator connected to the hub assembly and in fluid communication with the hemostatic valve; and
a sealed chamber including a closed-cell foam defined by the pressure regulator, the sealed chamber having an interior, wherein the interior of the sealed chamber is filled with a gas that is fluidly isolated from the hemostatic valve.

19. The introducer sheath according to claim 18, further comprising anchor wings mounted to a base of the assembly hub, the anchor wings configured to anchor the assembly hub to a vascular access site.

20. The introducer sheath according to claim 18, wherein the hemostatic valve includes a valve body and a collapsible member, and wherein the collapsible member is secured to the valve body by an O-ring.

* * * * *